(12) United States Patent
Agris

(10) Patent No.: US 8,609,609 B2
(45) Date of Patent: Dec. 17, 2013

(54) PEPTIDES AND METHODS OF USE AS THERAPEUTICS AND SCREENING AGENTS

(75) Inventor: Paul F. Agris, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 273 days.

(21) Appl. No.: 12/812,802

(22) PCT Filed: Jan. 16, 2009

(86) PCT No.: PCT/US2009/000297
§ 371 (c)(1),
(2), (4) Date: Oct. 13, 2010

(87) PCT Pub. No.: WO2009/091586
PCT Pub. Date: Jul. 23, 2009

(65) Prior Publication Data
US 2011/0098215 A1 Apr. 28, 2011

Related U.S. Application Data

(60) Provisional application No. 61/022,075, filed on Jan. 18, 2008.

(51) Int. Cl.
*A61K 38/00* (2006.01)
(52) U.S. Cl.
USPC .............. 514/3.8; 514/1.1; 530/300; 530/326; 530/328; 530/332
(58) Field of Classification Search
None
See application file for complete search history.

(56) References Cited

U.S. PATENT DOCUMENTS

| | | |
|---|---|---|
| 6,962,785 B2 | 11/2005 | Agris et al. |
| 2004/0031072 A1 | 2/2004 | La Rosa et al. |
| 2004/0082068 A1 | 4/2004 | Kleiman et al. |
| 2006/0002951 A1 | 1/2006 | Kleiman et al. |

FOREIGN PATENT DOCUMENTS

JP   08151396 A   *   6/1996

OTHER PUBLICATIONS

Galati et al. Z Naturforsch 2003.*
Kleiman, Life, 2002, 53: 107-114.*
Cen S et al. Human Lysyl-tRNA synthetase: a limiting factor for tRNALys packaging into HIV-1. Int. Conf. AIDS. Jul. 7, 2002. Abstract.
Eshete M et al. Specificity of phage display selected peptides for modified anticodon stem and loop domains of tRNA. The Protein Journal. Jan. 2007; 26(1): 61-73.
International Search Report and Written Opinion, PCT/US09/00297, mailed Jul. 23, 2009.
Database UNIPROT (Online). EBI accession No. UNIPROT:Q4RU97, Jul. 19, 2005, 1 pg.
Database USPTO Proteins (Online). EBI accession No. USPOP:AAU59913, Sep. 22, 2004, 1 pg.
Database UNIPROT: (Online). EBI accession No. UNIPROT:A5EJG1., Jun. 12, 2007, 1 pg.
Supplementary European Search Report, EP 09701723, Apr. 19, 2011.
Mak et al., Primer tRNAs for Reverse Transcription, Journal of Virology, 1997, pp. 8087-8095, vol. 71, No. 11.

* cited by examiner

*Primary Examiner* — Cecilia J Tsang
*Assistant Examiner* — Li Lee
(74) *Attorney, Agent, or Firm* — Myers Bigel Sibley & Sajovec, P.A.

(57) ABSTRACT

Host RNA/viral protein interaction as a target of intervention in the replication of viruses, e.g., the human immunodeficiency virus (HIV) are described. The target being upstream of the final replication product, and being crucial to the viral replication, is less likely to be genetically altered to drug resistance. Peptides that intervene in this RNA/viral protein interaction are also described, as well as compositions containing the same and methods of use thereof.

10 Claims, 9 Drawing Sheets

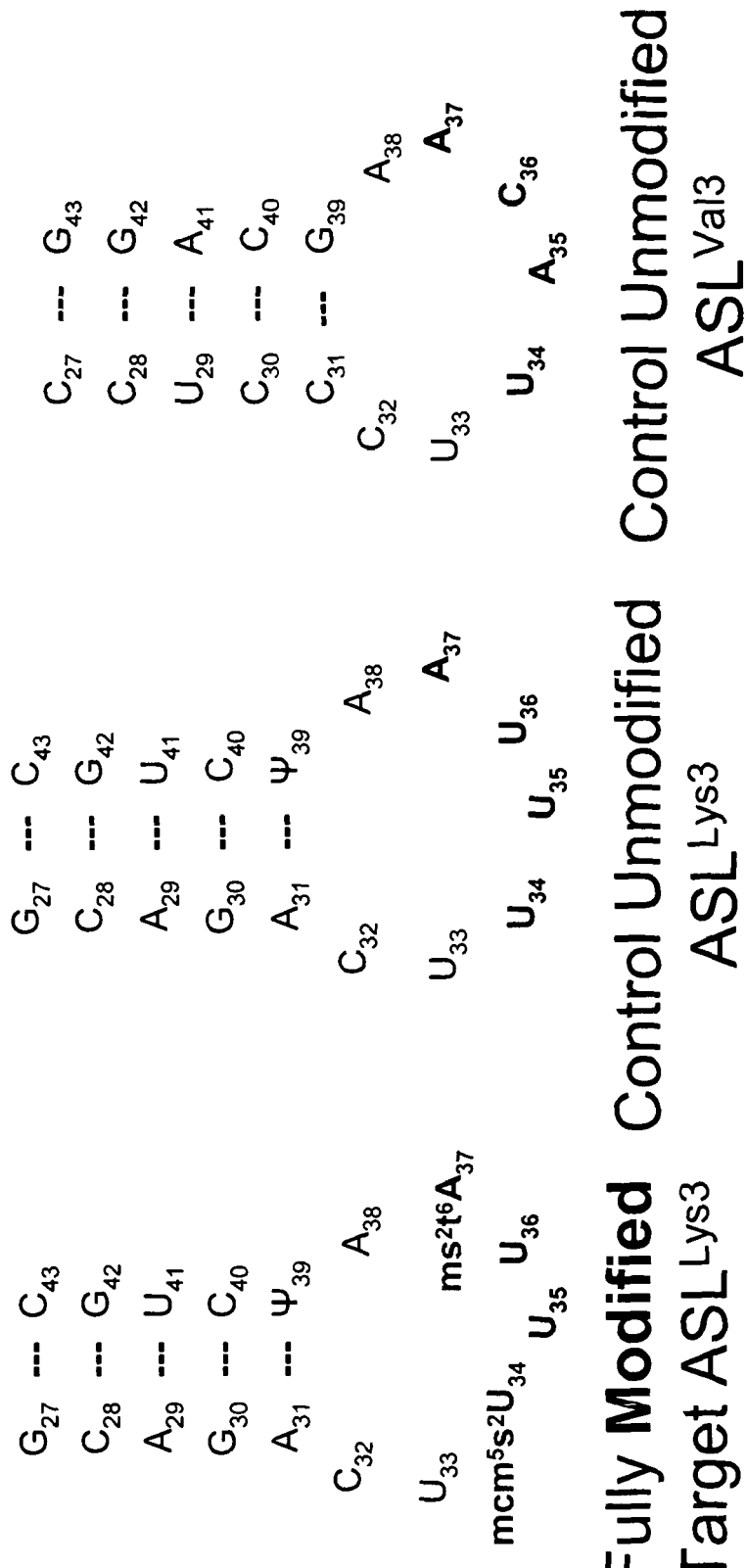
Figure 4. Anticodon stem and loop domains (ASL) of the fully modified human tRNA$^{Lys3}$, the primer of HIV reverse transcriptase, and control ASLs of the unmodified ASL$^{Lys3}$ and the unmodified *E. coli* ASL$^{Val3}$.

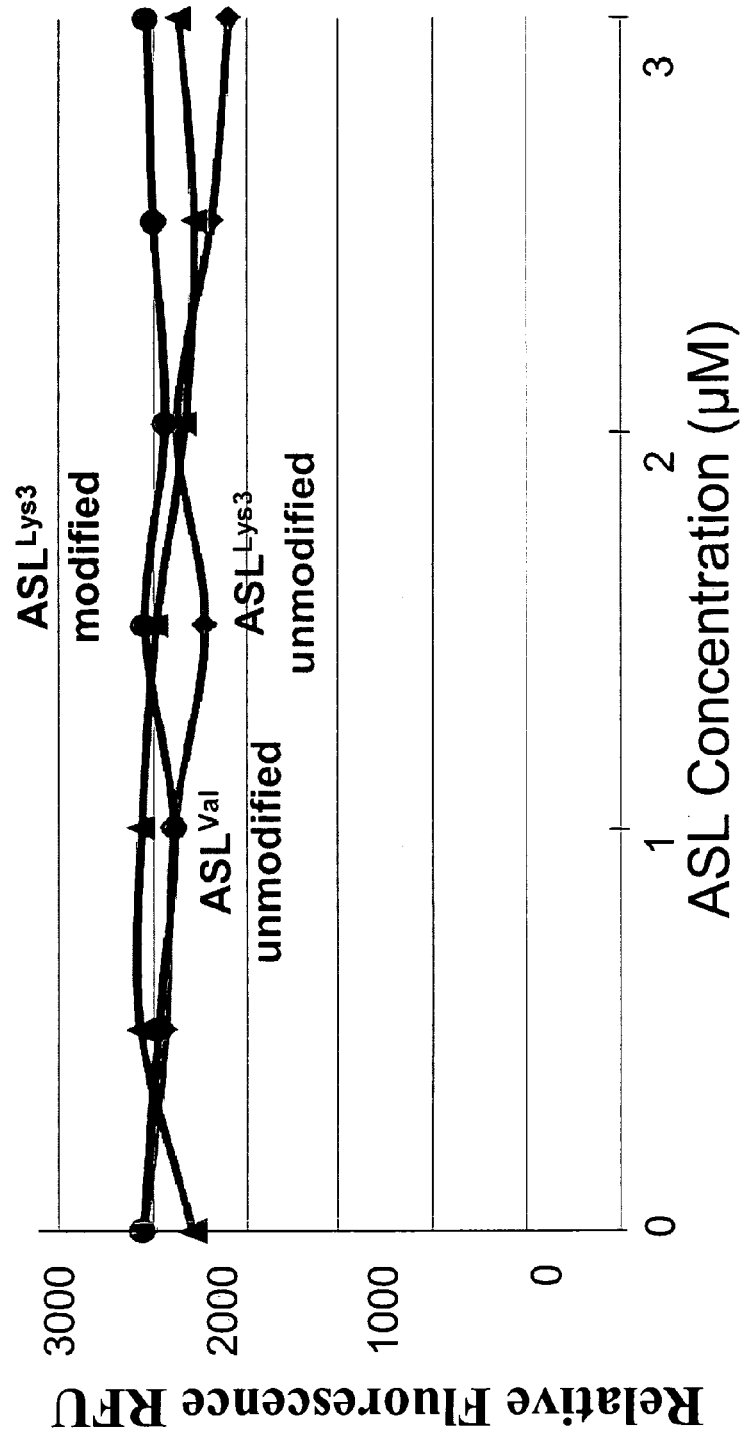
Figure 5. Control peptide does not bind the target modified ASL$^{Lys3}$, nor the control ASLs.

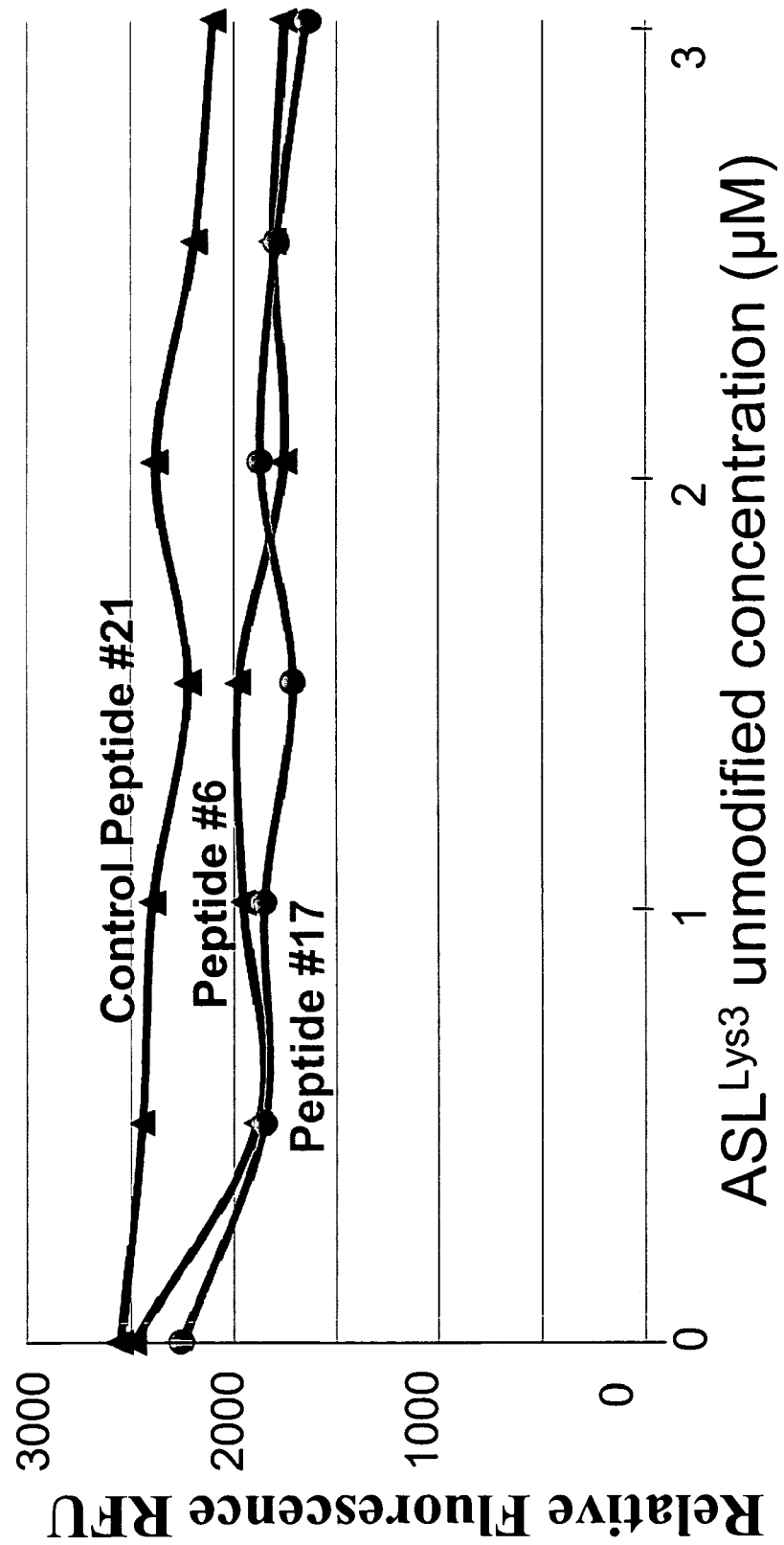
Figure 6. Experimental and control peptides do not exhibit binding to the unmodified ASL$^{Lys3}$.

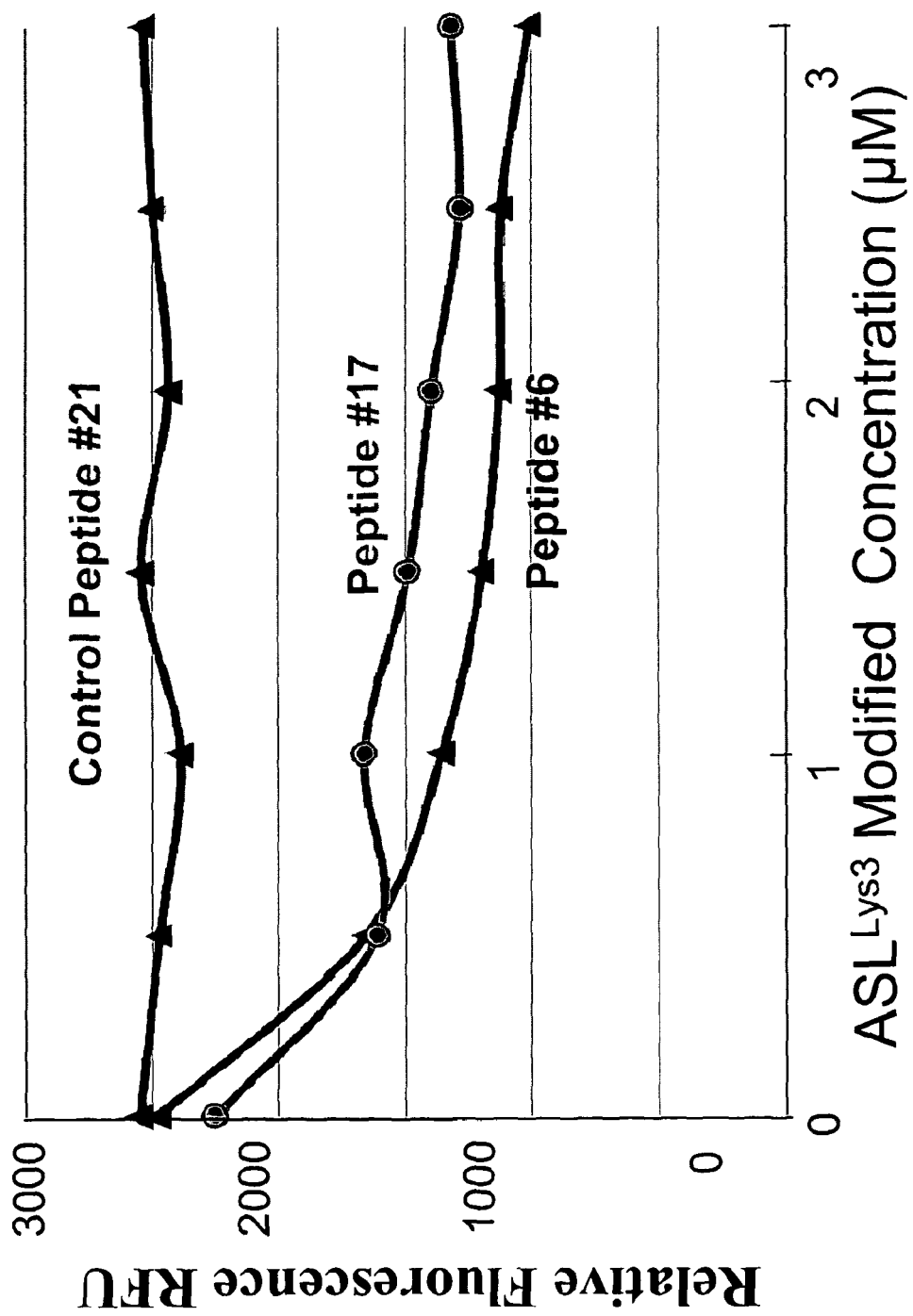
Figure 7. Experimental peptides bind to the modified ASL$^{Lys3}$

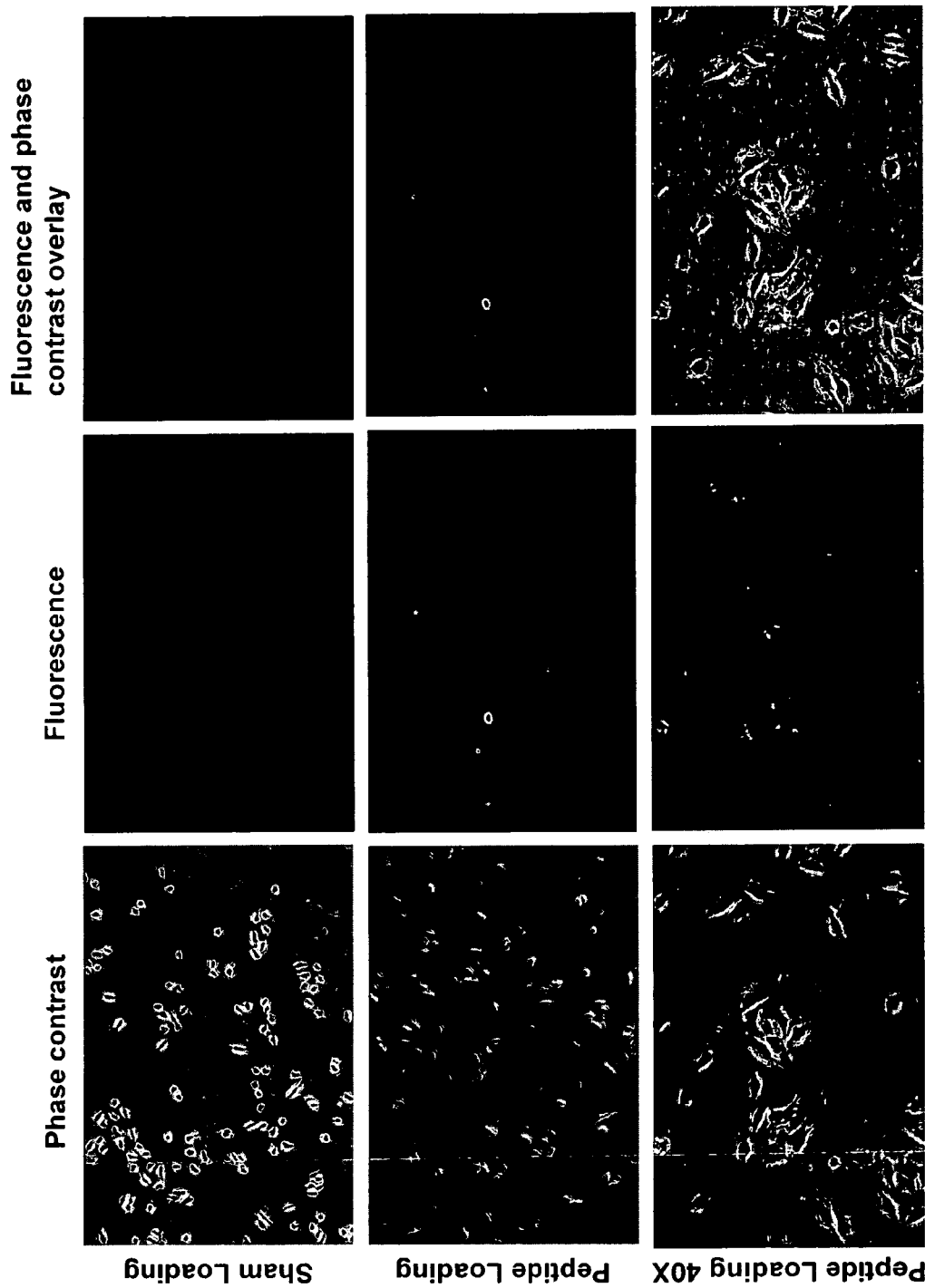
Figure 8. Feline cells loaded with fluorescein-conjugated peptide #6.

Figure 9. Feline cells infected with equine infectious anemia virus (EIAV) and loaded with fluorescein-conjugated peptide #6 have significantly reduced reverse transcriptase activity.

SEQUENCE LISTING

```
<160> NUMBER OF SEQ ID NOS: 24

<210> SEQ ID NO 1
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 1

Phe Ser Val Ser Phe Pro Ser Leu Pro Ala Pro Pro Asp Arg Ser
1               5                   10                  15

<210> SEQ ID NO 2
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 2

Gly Arg Val Thr Tyr Tyr Ser Cys Gly Val Ser Leu Leu Phe Gln
1               5                   10                  15

<210> SEQ ID NO 3
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 3

Ala Gly Pro Val Pro Leu His Ser Leu Ser Tyr Tyr Tyr Asn Gln
1               5                   10                  15

<210> SEQ ID NO 4
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 4

Arg Ala Val Met Thr Val Val Trp Pro Val Ser Phe Ala Gly Phe
1               5                   10                  15

<210> SEQ ID NO 5
<211> LENGTH: 15
<212> TYPE: PRT
<213> ORGANISM: Artificial
<220> FEATURE:
```

<223> OTHER INFORMATION: hASL LYS3 binding peptide

<400> SEQUENCE: 5

Arg Val Thr His His Ala Phe Leu Gly Ala His Arg Thr Val Gly
1               5                   10                  15

<210> SEQ ID NO 6
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 6

Pro Ala Val Ala Ser Thr Ser Ser Leu Ile Ile Asp Gly Pro Phe
1               5                   10                  15

<210> SEQ ID NO 7
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 7

Pro Lys Ala Phe Gln Tyr Gly Gly Arg Ala Val Gly Gly Leu Trp
1               5                   10                  15

<210> SEQ ID NO 8
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 8

Ala Ala His Val Ser Glu His Tyr Val Ser Gly Ser Leu Arg Pro
1               5                   10                  15

<210> SEQ ID NO 9
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 9

Ala Ser Val Gly Pro Ala Pro Trp Ala Met Thr Pro Pro Val Ser
1               5                   10                  15

<210> SEQ ID NO 10
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 10

Ala Pro Ala Leu Trp Tyr Pro Trp Arg Ser Leu Leu Pro Leu Tyr
1               5                   10                  15

<210> SEQ ID NO 11
<211> LENGTH: 15
<212> TYPE: PRT
<213> ORGANISM: Artificial
<220> FEATURE:
<223> OTHER INFORMATION: hASL LYS3 binding peptide

```
<400> SEQUENCE: 11

Ala Ser Leu His Pro Val Pro Lys Thr Trp Phe Phe Leu Leu Ser
1               5                   10                  15

<210> SEQ ID NO 12
<211> LENGTH: 15
<212> TYPE: PRT
<213> ORGANISM: Artificial
<220> FEATURE:
<223> OTHER INFORMATION: hASL LYS3 binding peptide

<400> SEQUENCE: 12

Trp Ser His Ser Arg Asn Thr Ala Asp Val Pro Val Ser Met Leu
1               5                   10                  15

<210> SEQ ID NO 13
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 13

His Arg Gly Tyr Cys Arg Asp Arg Val Val Asn Cys Gly Glu Tyr Phe
1               5                   10                  15

<210> SEQ ID NO 14
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 14

Pro His Arg Gln Cys Ser Ala Pro Ala Lys Ser Cys Lys Ile Leu Pro
1               5                   10                  15

<210> SEQ ID NO 15
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 15

Thr Leu Pro Ala Cys His Glu Leu Pro Lys His Cys Lys Arg Arg Gly
1               5                   10                  15

<210> SEQ ID NO 16
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 16

Thr Leu Pro Ala Cys His Glu Leu Pro Lys His Cys Asn Glu Ala Arg
1               5                   10                  15

<210> SEQ ID NO 17
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 17
```

-continued

```
Asn Gly Pro Glu Cys Asn Ala Tyr Met Val Arg Cys Arg Gly Tyr His
1               5                   10                  15
```

<210> SEQ ID NO 18
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 18

```
Gly Asn Ser Asn Cys Pro Met Leu Asn Glu Gln Cys Pro Trp Gln Asp
1               5                   10                  15
```

<210> SEQ ID NO 19
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 19

```
His Thr Glu Thr Cys Ile Asn Ile Arg Asn Thr Cys Thr Thr Val Ala
1               5                   10                  15
```

<210> SEQ ID NO 20
<211> LENGTH: 16
<212> TYPE: PRT
<213> ORGANISM: Artificial
<220> FEATURE:
<223> OTHER INFORMATION: hASL LYS3 binding peptide

<400> SEQUENCE: 20

```
Leu Lys Leu Pro Cys Lys Ile Thr Ile Asn Asn Cys Gln Leu Ala Gly
1               5                   10                  15
```

<210> SEQ ID NO 21
<211> LENGTH: 76
<212> TYPE: RNA
<213> ORGANISM: Homo sapiens
<220> FEATURE:
<221> NAME/KEY: misc_feature
<222> LOCATION: (27)..(27)
<223> OTHER INFORMATION: n is pseudouridine
<220> FEATURE:
<221> NAME/KEY: misc_feature
<222> LOCATION: (39)..(39)
<223> OTHER INFORMATION: n is pseudouridine
<220> FEATURE:
<221> NAME/KEY: misc_feature
<222> LOCATION: (54)..(54)
<223> OTHER INFORMATION: n is 5-methyluridine
<220> FEATURE:
<221> NAME/KEY: misc_feature
<222> LOCATION: (55)..(55)
<223> OTHER INFORMATION: n is pseudouridine

<400> SEQUENCE: 21
gcccggauag cucagdcggd agagcancag acuuuuaanc ugagggdcca gggnncaagu      60
cccuguucgg gcgcca                                                     76

<210> SEQ ID NO 22
<211> LENGTH: 17
<212> TYPE: RNA
<213> ORGANISM: Artificial
<220> FEATURE:
<223> OTHER INFORMATION: Synthetic modified target hASL Lys3 sequence
<220> FEATURE:
<221> NAME/KEY: misc_feature
<222> LOCATION: (8)..(8)

```
<223> OTHER INFORMATION: n is 5-methoxycarbonylmethyl-2-thiouridine
<220> FEATURE:
<221> NAME/KEY: misc_feature
<222> LOCATION: (11)..(11)
<223> OTHER INFORMATION: n is
      N-((9-beta-D-ribofuranosyl-2-methylthiopurine-6-yl)carbamoyl)thre
      onine
<220> FEATURE:
<221> NAME/KEY: misc_feature
<222> LOCATION: (13)..(13)
<223> OTHER INFORMATION: n is pseudouridine

<400> SEQUENCE: 22
gcagacunuu nancugc                                                    17

<210> SEQ ID NO 23
<211> LENGTH: 17
<212> TYPE: RNA
<213> ORGANISM: Artificial
<220> FEATURE:
<223> OTHER INFORMATION: Synthetic unmodified hASL Lys3 sequence
<220> FEATURE:
<221> NAME/KEY: misc_feature
<222> LOCATION: (13)..(13)
<223> OTHER INFORMATION: n is pseudouridine

<400> SEQUENCE: 23
gcagacuuuu aancugc                                                    17

<210> SEQ ID NO 24
<211> LENGTH: 17
<212> TYPE: RNA
<213> ORGANISM: Artificial
<220> FEATURE:
<223> OTHER INFORMATION: Synthetic unmodified hASL Val3 sequence

<400> SEQUENCE: 24
ccucccuuac aagcagg                                                    17
```

PEPTIDES AND METHODS OF USE AS THERAPEUTICS AND SCREENING AGENTS

RELATED APPLICATIONS

This application is a 35 U.S.C. §371 national phase application of PCT Application PCT/US2009/000297, filed Jan. 16, 2009, and published in English on Jul. 23, 2009, as International Publication No. WO 2009/091586, and which claims the benefit under 35 U.S.C. §119(e) of U.S. Provisional Patent Application Ser. No. 61/022,075, filed Jan. 18, 2008, the disclosure of each of which is incorporated herein by reference in its entirety.

STATEMENT OF GOVERNMENT SUPPORT

This invention was made with Government support under NIH grant 2R01 GM23037. The US Government has certain rights to this invention.

BACKGROUND

There are many different types of ribonucleic acids (RNAs) in cells. RNAs function in the synthesis of proteins. They are also involved in the replication of retroviruses, such as those involved in HIV and cancers. Because RNAs are the immediate products of genes, they also control the expression of genes. RNAs generally function through RNA-protein interactions, or RNA-RNA interactions, and because these functions are critical to virus viability, the replication of an infectious virus, or the progression of a human disease.

The general targeting of RNA/protein interactions is disclosed herein. The targeting of proteins and protein synthesis with synthetic drugs and natural products has been successful for a century, but does result in drug resistant targets. The targeting of RNA/RNA interactions has significant disadvantages because, e.g., the 'chemical space' of RNA is limited in the main to the four major bases, A, C, G and U. Even though native RNAs have some posttranscriptional modifications that enhance the chemical space for drug interaction, the RNA/RNA function is still one of hydrogen bond, base pairing in common with all of RNA structure and interactions.

In contrast, RNA/protein interactions are specific functional interactions involving a wealth of chemical interactions, to which highly specific drugs can be targeted. These interactions include hydrogen bonds, hydrophobic interactions, ionic interactions, salt bridges, and water bridges between the protein and the RNA.

SUMMARY

The invention provides a novel host RNA/viral protein interaction as a target of intervention in the replication of viruses, e.g., the human immunodeficiency virus (HIV). The target being upstream of the final replication product, and being crucial to the viral replication, is less likely to be genetically altered to drug resistance. Peptides that intervene in this crucial human RNA/viral protein interaction are disclosed herein. They (or related derivatives) can be used as tools to develop small molecule candidate drugs, and/or can be used directly as therapeutic agents.

A first aspect of the present invention is a peptide (sometimes also referred to as an "active compound" herein) comprising, consisting of or consisting essentially of one or more amino acid sequences. Sequences include: (a) the peptides set forth in Table 1 herein; (b) a fragment (e.g., of 10 or more contiguous amino acids) from an amino acid sequence of Table 1 herein; and (c) an amino acid sequence that is homologous (e.g., at least about 50% homologous) to an amino acid sequence of Table 1 herein.

A further aspect of the invention is a nucleic acid molecule encoding a peptide as described above, along with vectors and host cells comprising the same.

A further aspect of the invention is a composition comprising a peptide as described herein in a pharmaceutically acceptable carrier, diluent or excipient.

A further aspect of the invention is a therapeutic composition for treatment or prevention of a retroviral infection comprising, consisting of or consisting essentially of at least one peptide that interferes with the ability of a protein, nucleic acid or metabolite to recruit host $tRNA^{LYS3}$ for reverse transcription and a pharmaceutically acceptable carrier, diluent or excipient, along with methods of treating a subject infected with a retrovirus by administering the subject such a composition, e.g., in an amount effective to treat the infection).

A further aspect of the invention is a method of treating a retroviral infection in a subject in need thereof, comprising administering said subject a peptide or active compound as described herein in a treatment effective amount.

A further aspect of the invention is the use of a peptide or active compound as described herein for the preparation of a medicament for the treatment of a retroviral infection in a subject in need thereof.

A still further aspect of the invention is the use of a peptide or active compound as described herein for the treatment of a retroviral infection in a subject in need thereof.

A further aspect of the invention is a method of screening for a compound or biologic for treatment of a retroviral infection, comprising: contacting a $tRNA^{LYS3}$ with at least one peptide that interacts with $tRNA^{LYS3}$; contacting said $tRNA^{LYS3}$ and said at least one peptide with one or more candidate compounds; and identifying the one or more candidate compounds that inhibit the interaction of $tRNA^{LYS3}$ with the at least one peptide.

A further aspect of the invention is a method of screening for a therapeutic compound or biologic for treatment of a retroviral infection, comprising: contacting a $tRNA^{LYS3}$ with one or more compounds and at least one reporter peptide; and identifying compounds that bind to $tRNA^{LYS3}$.

Thus the present invention provides, among other things, the following:

1. A peptide comprising one or more amino acid sequences selected from: (a) FSVSFPSLPAPPDRS (SEQ ID NO.: 1), GRVTYYSCGVSLLFQ (SEQ ID NO.: 2), AGPVPLHSLSYYYNQ (SEQ ID NO.: 3), RAVMTVVWPVSFAGF (SEQ ID NO.: 4), RVTHHAFLGAHRTVG (SEQ ID NO.: 5), PAVASTSSLIIDGPF (SEQ ID NO.: 6), PKAFQYGGRAVGGLW (SEQ ID NO.: 7), AAHVSEHYVSGSLRP (SEQ ID NO.: 8), ASVGPAPWAMTPPVS (SEQ ID NO.: 9), APALWYPWRSLLPLY (SEQ ID NO.: 10), ASLHPVPKTWFFLLS (SEQ ID NO.: 11), WSHSRNTADVPVSML (SEQ ID NO.: 12), HRGYCRDRVVNCGEYF (SEQ ID NO.: 13), PHRQCSAPAKSCKILP (SEQ ID NO.: 14), TLPACHELPKHCKRRG (SEQ ID NO.: 15), TLPACHELPKHCNEAR (SEQ ID NO.: 16), NGPECNAYMVRCRGYH (SEQ ID NO.: 17), GNSNCPMLNEQCPWQD (SEQ ID NO.: 18), HTETCINIRNTCTTVA (SEQ ID NO.: 19), and LKLPCKITNNCQLAG (SEQ ID NO.: 20); (b) a fragment of 10 or more contiguous amino acids from an amino acid sequence of SEQ ID NOs.: 1-20; or (c) an amino acid sequence that is at least about 50% homologous to an amino acid sequence of SEQ ID NOs.: 1-20.

2. The peptide of 1, wherein said fragment of 10 or more contiguous amino acids is functionally equivalent to the corresponding amino acid sequence of SEQ ID NO.: 1-20.
3. The peptide of 1, wherein said homologous amino acid sequence is functionally equivalent to the corresponding amino acid sequence of SEQ ID NO.: 1-20.
4. The peptide of any one of 1-3, wherein the peptide is at least about 10 amino acids in length, 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length.
5. The peptide of any one of 1-4, wherein the peptide is less than about 12 amino acids in length, less than about 15 amino acids in length, less than about 20 amino acids in length, less than about 25 amino acids in length, less than about 30 amino acids in length, less than about 35 amino acids in length, less than about 40 amino acids in length, less than about 50 amino acids in length, less than about 60 amino acids in length, less than about 70 amino acids in length, less than about 80 amino acids in length, less than about 90 amino acids in length, less than about 100 amino acids in length, or less than about 150 amino acids in length.
6. The peptide of any one of 1-5, wherein the peptide contains an amino acid analog or derivative.
7. The peptide of any one of 1-6, wherein said homologous amino acid sequence is at least about 95% homologous to an amino acid sequence from the group of amino acid sequences consisting of SEQ ID NOs.: 1-20.
8. The peptide of any one of 1-6, wherein said homologous amino acid sequence is at least about 99% homologous to an amino acid sequence from the group of amino acid sequences consisting of SEQ ID NOs.: 1-20.
9. The peptide of any one of 1-8, wherein the peptide is modified to exhibit increased serum half life compared to an unmodified peptide.
10. The peptide of any one of 1-9, wherein said peptide is a D-amino acid.
11. The peptide of any one of 1-10, wherein the peptide is capable of interfering with the ability of a virus to use host tRNA$^{LYS3}$ to prime reverse transcription.
12. The peptide of any one of 1-11, wherein the peptide interferes with the ability of a viral protein to recruit tRNA$^{LYS3}$ in viral reverse transcription.
13. The peptide of any one of 1-12, wherein the peptide interferes with the ability of a host protein to assist in the recruitment of tRNA$^{LYS3}$ in viral reverse transcription.
14. The peptide of any one of 1-13, wherein the peptide is capable of interfering with the ability of tRNA$^{LYS3}$ to prime reverse transcription in vivo or in vitro.
15. The peptide of any one of 1-14, wherein said peptide inhibits tRNA$^{LYS3}$ annealing or priming on a viral genome thereby reducing viral replication.
16. The peptide of any one of 1-15, wherein said peptide binds to an anticodon stem loop structure of tRNA$^{LYS3}$.
17. The peptide of any one of 1-16, wherein said peptide prevents the viral protein from binding to an anticodon stem loop domain of the tRNA$^{LYS3}$.
18. The peptide of any one of 1-17, wherein said peptide is isolated.
19. The peptide of any one of 1-18, wherein said peptide is purified.
20. The isolated peptide of 18, wherein said peptide is effective as a prophylactic for treatment of a retroviral infection in a subject.
21. The isolated peptide of 18, wherein said peptide is effective for the prevention of a retroviral infection in a subject.
22. The isolated peptide of 20 or 21, wherein said retroviral infection is a lentivirus infection.
23. The isolated peptide of 22, wherein said lentivirus infection is a human immunodeficiency virus (HIV) infection.
24. The isolated peptide of 18, wherein said retroviral infection is selected from the group comprising HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection.
25. The isolated peptide of 18, wherein said lentivirus infection is selected from the group comprising HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection.
26. A fusion protein comprising the peptide of any one of 1-25.
27. A nucleic acid molecule encoding the peptide of any one of 1-26.
28. A vector comprising the nucleic acid molecule of 27.
29. A host cell comprising the vector of 28.
30. A host cell comprising the nucleic acid molecule of 27.
31. A therapeutic composition comprising the peptide of any one of 1-26 and a pharmaceutically acceptable carrier, diluent or excipient.
32. A therapeutic composition for treatment or prevention of a retroviral infection comprising at least one peptide that interferes with the ability of a protein, nucleic acid or metabolite to recruit host tRNA$^{LYS3}$ for reverse transcription and a pharmaceutically acceptable carrier, diluent or excipient.
33. The therapeutic composition of 32, wherein the protein, nucleic acid or metabolite is a retroviral protein, nucleic acid, metabolite or a fragment or subunit thereof.
34. The therapeutic composition of 33, wherein the retroviral protein is selected from the group comprising HIV polyprotein, reverse transcriptase, nucleocapsid protein, gag protein, protease, integrase, env protein, p24, gp41, gp120, gp140, gp160, rev, nef, and pol.

35. The therapeutic composition of 33, wherein said retroviral nucleic acid is selected from the group comprising HIV polyprotein, reverse transcriptase, nucleocapsid protein, gag protein, protease, integrase, env protein, p24, gp41, gp120, gp140, gp160, rev, nef, and pol.

36. The therapeutic composition of 33, wherein said retroviral protein, nucleic acid, metabolite or a fragment or subunit thereof is a lentivirus protein, nucleic acid, metabolite or a fragment or subunit thereof.

37. The therapeutic composition of 36, wherein said lentivirus protein, nucleic acid, metabolite or a fragment or subunit thereof is an HIV protein, nucleic acid, metabolite or a fragment or subunit thereof 38. The therapeutic composition of 32, wherein said protein, nucleic acid or metabolite is a host protein, nucleic acid, metabolite or a fragment or subunit thereof 39. The therapeutic composition of 36, wherein said host is a mammal.

40. The therapeutic composition of 39, wherein said host is a human.

41. The therapeutic composition of 38, wherein said host protein is lysyl-tRNA synthetase.

42. The therapeutic composition of 32, wherein said at least one peptide is a heterologous peptide.

43. The therapeutic composition of 32, wherein said peptide binds to an anticodon stem loop structure of $tRNA^{LYS3}$.

44. The therapeutic composition of 32, wherein said peptide prevents the protein, nucleic acid or metabolite from binding to an anticodon stem loop domain of the $tRNA^{LYS3}$.

45. A method of treating a subject infected with a retrovirus, comprising administering a therapeutic composition of 31 or 32.

46. The method of 45, wherein said retrovirus is selected from the group comprising HIV, simian immunodeficiency virus, equine infectious anemia virus, feline immunodeficiency virus, bovine immunodeficiency virus, murine leukemia virus, hepatitis C virus, avian leucosis virus, feline leukemia virus, bovine leukemia virus, human T-lymphotropic virus, Walleye dermal sarcoma virus, chimpanzee foamy virus, caprine arthritis-encephalomyelitis virus, and maedi-visna virus.

47. The method of 45, wherein said retrovirus is a lentivirus.

48. The method of 47, wherein said lentivirus is selected from the group comprising HIV, simian immunodeficiency virus, equine infectious anemia virus, feline immunodeficiency virus, bovine immunodeficiency virus, caprine arthritis-encephalomyelitis virus, and maedi-visna virus.

49. The method of 47, wherein said lentivirus is HIV.

50. The method of 45, wherein administration of said therapeutic composition reduces viral load in said subject by at least about 5%, at least about 10%, at least about 20%, at least about 30%, at least about 40%, at least about 50%, at least about 60%, at least about 70%, at least about 80%, at least about 90%, or at least about 99%.

51. The method of 45, wherein administration of said therapeutic composition increases CD4 levels by at least about 5%, at least about 10%, at least about 20%, at least about 30%, at least about 40%, at least about 50%, at least about 60%, at least about 70%, at least about 80%, at least about 90%, or about 100%.

52. A method of screening for a compound for treatment of a retroviral infection, comprising:
    contacting a $tRNA^{LYS3}$ with at least one peptide that interacts with $tRNA^{LYS3}$;
    contacting said $tRNA^{LYS3}$ and said at least one peptide with one or more candidate compounds; and
    identifying the one or more candidate compounds that inhibit the interaction of $tRNA^{LYS3}$ with the at least one peptide.

53. The method of 52, wherein contacting $tRNA^{LYS3}$ and said at least one peptide with one or more compounds occurs in vitro.

54. The method of 52, wherein $tRNA^{LYS3}$ and the at least one peptide are capable of binding.

55. The method of 54, wherein said one or more candidate compounds inhibit the binding of $tRNA^{LYS3}$ with the at least one peptide.

56. The method of 52, wherein the $tRNA^{LYS3}$ is an anticodon stem loop domain of $tRNA^{LYS3}$.

57. The method of 56, wherein said anticodon stem loop domain of $tRNA^{LYS3}$ contains one or more modified nucleoside bases.

58. The method of 57, wherein said anticodon stem loop domain of $tRNA^{LYS3}$ contains two modified nucleoside bases.

59. The method of 58, wherein said anticodon stem loop domain of $tRNA^{LYS3}$ contains a 5-methoxymethyl-2-thiouridine at position 34 and a 2-methylthio-N-6-threonylcarbamoyladenosine at position 37.

60. The method of 52, wherein the at least one peptide is capable of recruiting $tRNA^{LYS3}$ for viral replication.

61. The method of 52, wherein the at least one peptide interferes with the ability of a viral protein to recruit $tRNA^{LYS3}$ in viral reverse transcription.

62. The method of 52, wherein the at least one peptide interferes with the ability of a host protein to assist in the recruitment of $tRNA^{LYS3}$ in viral reverse transcription.

63. The method of 52, wherein the at least one peptide is capable of interfering with the ability of $tRNA^{LYS3}$ to prime reverse transcription in vivo or in vitro.

64. The method of 52, wherein the at least one peptide inhibits $tRNA^{LYS3}$ annealing or priming on a viral genome thereby reducing viral replication.

65. The method of 52, wherein the at least one peptide binds to an anticodon stem loop structure of $tRNA^{LYS3}$.

66. The method of 52, wherein the at least one peptide prevents the viral protein from binding to an anticodon stem loop domain of the $tRNA^{LYS3}$.

67. The method of 52, wherein said at least one peptide is a mimetic peptide.

68. The method of 67, wherein said mimetic peptide mimics a protein that binds to $tRNA^{LYS3}$ in a viral infection.

69. The method of 67, wherein said mimetic peptide is a viral protein mimetic peptide.

70. The method of 69, wherein said mimetic peptide mimics a protein selected from the group of viral proteins consisting of HIV polyprotein, reverse transcriptase, nucleocapsid protein, gag protein, protease, integrase, env protein, p24, gp41, gp120, gp140, gp160, rev, nef and pol.

71. The method of 67, wherein said mimetic peptide is a host protein mimetic peptide.

72. The method of 71, wherein said mimetic peptide is a host lysyl-tRNA mimetic protein.

73. The method of 52, wherein said at least one peptide comprises one or more amino acid sequences selected from:

(a) FSVSFPSLPAPPDRS (SEQ ID NO.: 1), GRVTYY-SCGVSLLFQ (SEQ ID NO.: 2), AGPVPLHSL-SYYYNQ (SEQ ID NO.: 3), RAVMTVVWPVSFAGF (SEQ ID NO.: 4), RVTHHAFLGAHRTVG (SEQ ID NO.: 5), PAVASTSSLIIDGPF (SEQ ID NO.: 6), PKAF-QYGGRAVGGLW (SEQ ID NO.: 7), AAHVSE-HYVSGSLRP (SEQ ID NO.: 8), ASVGPAPWAMTP-PVS (SEQ ID NO.: 9), APALWYPWRSLLPLY (SEQ ID NO.: 10), ASLHPVPKTWFFLLS (SEQ ID NO.: 11), WSHSRNTADVPVSML (SEQ ID NO.: 12), HRGYCRDRVVNCGEYF (SEQ ID NO.: 13), PHRQCSAPAKSCKILP (SEQ ID NO.: 14), TLPACH-ELPKHCKRRG (SEQ ID NO.: 15), TLPACHELPKH-CNEAR (SEQ ID NO.: 16), NGPECNAYMVRCR-GYH (SEQ ID NO.: 17), GNSNCPMLNEQCPWQD (SEQ ID NO.: 18), HTETCINIRNTCTTVA (SEQ ID NO.: 19), and LKLPCKITINNCQLAG (SEQ ID NO.: 20); or (b) a fragment of 10 or more contiguous amino acids from an amino acid sequence of SEQ ID NOs.: 1-20; or (c) an amino acid sequence that is at least about 90% homologous to an amino acid sequence of SEQ ID NOs.: 1-20.

74. The method of 52, wherein said at least one peptide is labeled.

75. The method of 74, wherein said at least one peptide is fluorescently labeled.

76. The method of 75, further comprising detecting fluorescence after contacting said tRNA$^{LYS3}$ and said at least one peptide with one or more candidate compounds, wherein a change in fluorescence is indicative of a compound or biologic that binds said tRNA$^{LYS3}$ and/or said at least one peptide.

77. The method of 75, further comprising detecting fluorescence after contacting said tRNA$^{LYS3}$ and said at least one peptide with one or more candidate compounds, wherein a change in fluorescence is indicative of a compound or biologic that inhibits the binding of said tRNA$^{LYS3}$ and said at least one peptide.

78. The method of 76 or 77, wherein a change in fluorescence is indicative of a compound or biologic effective for the treatment or prevention of a retroviral infection.

79. The method of 78, wherein said retroviral infection is selected from the group comprising HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection.

80. The method of 78, wherein said retroviral infection is a lentivirus infection.

81. The method of 80, wherein said lentivirus infection is selected from the group comprising HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection.

82. The method of 74, wherein said at least one peptide is labeled with biotin.

83. The method of 82, wherein said at least one biotin-labeled peptide is bound to a solid support coated with avidin.

84. A method of screening for a therapeutic compound for treatment of a retroviral infection, comprising: contacting a tRNA$^{LYS3}$ with one or more compounds and at least one reporter peptide; and identifying compounds that bind to tRNA$^{LYS3}$.

85. The method of 84, wherein said tRNA$^{LYS3}$ that contacts said one or more compounds is a tRNA$^{LYS3}$ anticodon stem loop domain.

86. The method of 85, wherein said anticodon stem loop domain of tRNA$^{LYS3}$ contains one or more modified nucleoside bases.

87. The method of 86, wherein said anticodon stem loop domain of tRNA$^{LYS3}$ contains two modified nucleoside bases.

88. The method of 86, wherein said anticodon stem loop domain of tRNA$^{LYS3}$ contains a 5-methoxymethyl-2-thiouridine at position 34 and a 2-methylthio-N-6-threo-nylcarbamoyladeno sine at position 37.

89. The method of 56 or 85, wherein said tRNA$^{LYS3}$ anticodon stem loop domain is a human tRNA$^{LYS3}$ anticodon stem loop domain.

90. The method of 84, wherein said reporter peptide comprises a detection moiety.

91. The method of 90, wherein said detection moiety is a fluorescence moiety.

92. The method of 90, wherein said reporter peptide is capable of interacting with said tRNA$^{LYS3}$ in the absence of said one or more compounds.

93. The method of 92, wherein said fluorescence moiety fluoresces differently when said reporter peptide interacts with said tRNA$^{LYS3}$ compared to when said reporter peptide does not interact with said tRNA$^{LYS3}$.

94. The method of 90, wherein said reporter peptide is capable of binding with said tRNA$^{LYS3}$ in the absence of said one or more compounds.

95. The method of 94, wherein said fluorescence moiety fluoresces differently when said reporter peptide binds to said tRNA$^{LYS3}$ compared to when said reporter peptide does not bind to said tRNA$^{LYS3}$.

96. The method of 84, wherein said reporter peptide is a mimetic peptide.

97. The method of 96, wherein said mimetic peptide mimics a protein that binds to tRNA$^{LYS3}$ in a viral infection.

98. The method of 96, wherein said mimetic peptide is a viral protein mimetic peptide.

99. The method of 98, wherein said mimetic peptide mimics a protein selected from comprising HIV polyprotein, reverse transcriptase, nucleocapsid protein, gag protein, protease, integrase, env protein, p24, gp41, gp120, gp140, gp160, rev, nef and pol.

100. The method of 96, wherein said mimetic peptide is a host protein mimetic peptide.

101. The method of 100, wherein said mimetic peptide is a host lysyl-tRNA mimetic protein.

102. The method of 84, wherein said reporter peptide comprises an amino acid sequence selected from:

(a) FSVSFPSLPAPPDRS (SEQ ID NO.: 1), GRVTYY-SCGVSLLFQ (SEQ ID NO.: 2), AGPVPLHSL-SYYYNQ (SEQ ID NO.: 3), RAVMTVVWPVSFAGF (SEQ ID NO.: 4), RVTHHAFLGAHRTVG (SEQ ID NO.: 5), PAVASTSSLIIDGPF (SEQ ID NO.: 6), PKAF-QYGGRAVGGLW (SEQ ID NO.: 7), AAHVSE-HYVSGSLRP (SEQ ID NO.: 8), ASVGPAPWAMTP-PVS (SEQ ID NO.: 9), APALWYPWRSLLPLY (SEQ

ID NO.: 10), ASLHPVPKTWFFLLS (SEQ ID NO.: 11), WSHSRNTADVPVSML (SEQ ID NO.: 12), HRGYCRDRVVNCGEYF (SEQ ID NO.: 13), PHRQCSAPAKSCKILP (SEQ ID NO.: 14), TLPACHELPKHCKRRG (SEQ ID NO.: 15), TLPACHELPKHCNEAR (SEQ ID NO.: 16), NGPECNAYMVRCRGYH (SEQ ID NO.: 17), GNSNCPMLNEQCPWQD (SEQ ID NO.: 18), HTETCINIRNTCTTVA (SEQ ID NO.: 19), and LKLPCKITINNCQLAG (SEQ ID NO.: 20); or (b) a fragment of 10 or more contiguous amino acids from an amino acid sequence of SEQ ID NOs.: 1-20; or (c) an amino acid sequence that is at least about 90% homologous to an amino acid sequence of SEQ ID NOs.: 1-20.

103. The method of 84, wherein said at least one reporter peptide is two or more reporter peptides, each reporter peptide with a different detection moiety.

104. The method of 84, wherein said retroviral infection is selected from the group comprising HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection.

105. The method of 84, wherein said retroviral infection is a lentivirus infection.

106. The method of 105, wherein said lentivirus infection is selected from the group comprising HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection.

107. A method of treating a retroviral infection in a subject in need thereof, comprising administering said subject an effective amount of the peptide of any one of 1-21.

108. The method of 107, wherein said retroviral infection is a lentivirus infection.

109. The method of 108, wherein said lentivirus infection is a human immunodeficiency virus (HIV) infection.

110. The method of 107, wherein said retroviral infection is selected from the group comprising HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection.

111. The method of 107, wherein said lentivirus infection selected from the group comprising HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection.

112. A use of a peptide of any one of 1-21 for the preparation of a medicament for the treatment of a retroviral infection in a subject in need thereof.

113. The use of 112, wherein said retroviral infection is a lentivirus infection.

114. The use of 113, wherein said lentivirus infection is a human immunodeficiency virus (HIV) infection.

115. The use of 112, wherein said retroviral infection is selected from the group comprising HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection.

116. The use of 113, wherein said lentivirus infection is selected from the group comprising HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection.

117. A use of a peptide of any one of 1-21 for the treatment of a retroviral infection in a subject in need thereof.

118. The use of 117, wherein said retroviral infection is a lentivirus infection.

119. The use of 118, wherein said lentivirus infection is a human immunodeficiency virus (HIV) infection.

120. The use of 117, wherein said retroviral infection is selected from the group comprising HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection.

121. The use of 118, wherein said lentivirus infection is elected from the group comprising HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection.

122. The composition of any one of 31-44, further comprising at least one additional anti-viral active agent.

123. The composition of 122, wherein said at least one additional anti-viral active agent is selected from the group consisting of entry inhibitors, HIV-protease inhibitors, nucleoside reverse transcriptase inhibitors, non-nucleoside reverse transcriptase inhibitors, and integrase inhibitors.

BRIEF DESCRIPTION OF THE DRAWINGS

FIG. 4. Anticodon stem and loop domains (ASL) of the fully modified human tRNA$^{LYS3}$ (SEQ ID NO:22), the primer of HIV reverse transcriptase, and control ASLs of the unmodified ASL$^{LYS3}$ (SEQ ID NO:23) and the unmodified E. coli ASL$^{LYS3}$ (SEQ ID NO:24).

FIG. 5. Control peptide does not bind the target modified ASL$^{LYS3}$, nor the control ASLs.

FIG. 6. Experimental and control peptides do not exhibit binding to the unmodified ASL$^{LYS3}$.

FIG. 7. Experimental peptides bind to the modified ASL$^{LYS3}$.

FIG. 8. Feline cells loaded with fluorescein-conjugated peptide #6. Feline (FEA) cells are "shear-loaded" with the peptide #6 that binds the modified ASL$^{LYS3}$.

FIG. 9. Feline cells infected with equine infectious anemia virus (EIAV) and loaded with fluorescein-conjugated peptide #6 have significantly reduced reverse transcriptase activity.

DETAILED DESCRIPTION

Figure 1:
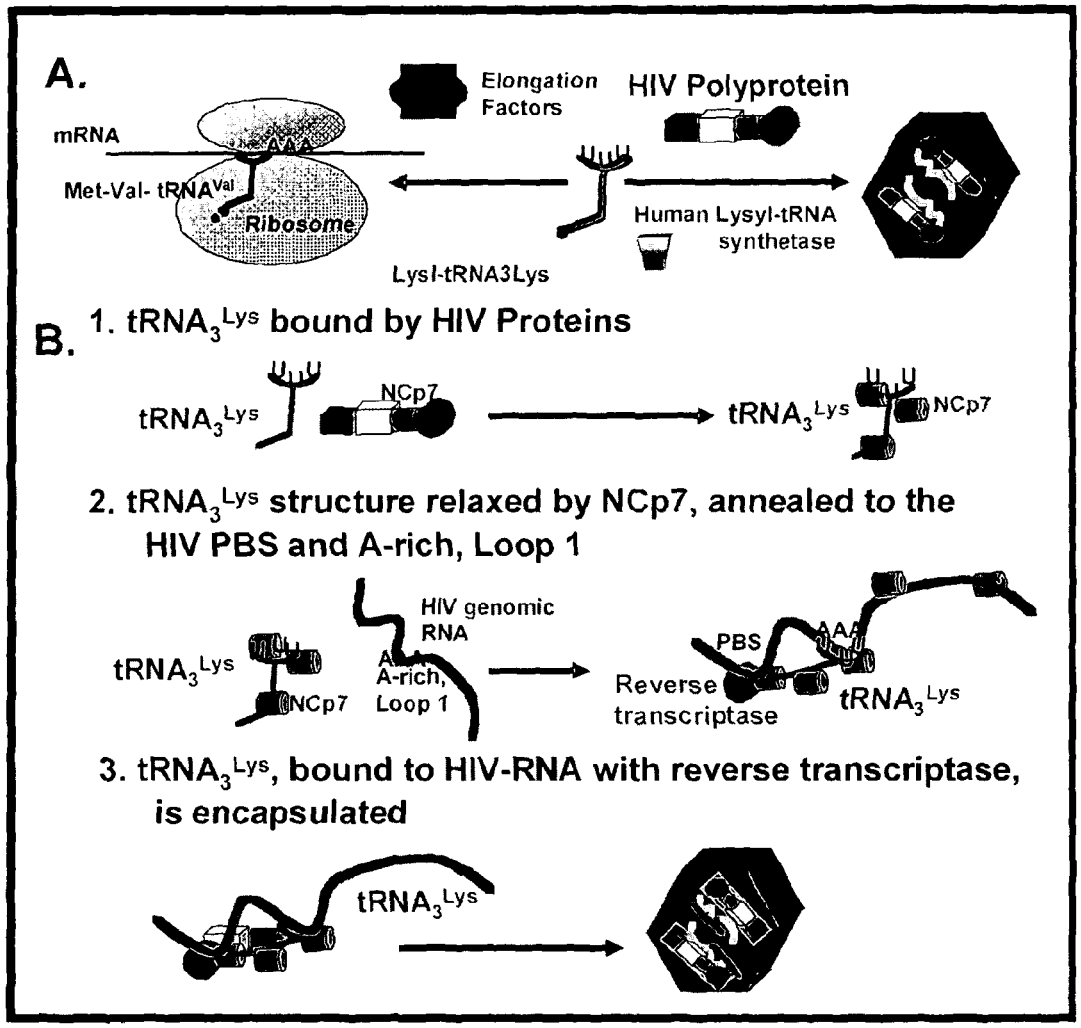
FIG. 1: HIV recruitment of human tRNA$^{LYS3}$.

The present disclosure features, inter alia, peptides with SEQ ID NOs: 1-20, fragments of such peptides, and amino acid sequences homologous, e.g., 90% homologous to such peptides. The featured peptides can bind to tRNA, e.g., tRNA$^{LYS3}$ and, e.g., prevent use of such tRNA by viruses, e.g., HIV, that infect cells. The disclosure also features therapeutic compositions that include at least one peptide that interferes with the ability of a protein, nucleic acid, or metabolite to recruit tRNA, e.g., tRNA$^{LYS3}$. Methods of screening for compounds or biologics for treatment of viral, e.g., retroviral, infection are also featured. The methods can include contacting tRNA, e.g., tRNA$^{LYS3}$, with at least one peptide that interacts with tRNA, contacting the tRNA and the peptide with a candidate compound or biologic, and identifying a compound or biologic that inhibits the interaction of tRNA with at least one peptide.

Definitions.

Subjects to be treated by the methods of the present invention are, in general, mammalian and primate subjects (human, monkey, ape, chimpanzee). Subjects may be male or female and may be of any age, including prenatal (i.e., in utero), neonatal, infant, juvenile, adolescent, adult, and geriatric subjects.

"Retroviral infection" as used herein refers to any retroviral infection, including but not limited to HIV infection, simian immunodeficiency virus infection, equine infectious anemia virus infection, feline immunodeficiency virus infection, bovine immunodeficiency virus infection, murine leukemia virus infection, hepatitis C virus infection, avian leucosis virus infection, feline leukemia virus infection, bovine leukemia virus infection, human T-lymphotropic virus infection, Walleye dermal sarcoma virus infection, chimpanzee foamy virus infection, caprine arthritis-encephalomyelitis virus infection, and maedi-visna virus infection. For some embodiments, lentiviral infections are preferred.

"Lentiviral infection" as used herein refers to any lentiviral infection, including but not limited to HIV infection, simian immunodeficiency virus infection, equine infectious anemia virus infection, feline immunodeficiency virus infection, bovine immunodeficiency virus infection, caprine arthritis-encephalomyelitis virus infection, and maedi-visna virus infection. In some embodiments, HIV invection is preferred.

"HIV infection" as used herein is intended to include infection with all subtypes thereof, including but not limited to HIV subtypes A, B, C, D, E, F, G, and O, and HIV-2.

"Peptide" is used herein as a generic term to refer to an isolated or synthetic full-length protein or oligopeptide having a minimum size of 2 amino acids.

"Amino acid" is used herein to denote a single amino acid and/or analogs; and/or modified forms thereof.

In certain embodiments, the peptide of this invention has a structure as described by SEQ ID NOS: 1-20 or a functional analog thereof. Such functional analogs of SEQ ID NOS. 1-20 include functional fragments truncated at the C-terminus by from 1 to 10 amino acids, including by 1, 2, 3, 4, or up to about 5 amino acids (with respect to SEQ ID NOS. 1-20). Such functional analogs may contain from 1 to 10 amino acid insertions, deletions, and/or substitutions (collectively) with respect to the native sequence, and in each case retaining the activity of the peptide. Such activity may be confirmed or assayed using any available assay.

The peptide chains may further include conservative amino acid substitutions (e.g., substitution in the mimetic with respect to the peptide of interest, or with respect to amino acid sequences disclosed herein). Conservative substitution tables providing functionally similar amino acids are well known in the art (Geysen et al., *Journal of Molecular Recognition*, 1:32-41, 1988). Conservative substitutions may include substitutions between aliphatic amino acids (e.g., G, A, I, L, or V); substitutions between aromatic amino acids (e.g., F, W, Y), substitutions between aliphatic polar-uncharged groups (e.g., C, S, T, M, N, or Q); substitutions between basic residues (e.g., K, R, or H); substitutions between amino acids with an acidic side chain (e.g., E or D), or with its uncharged counterpart (e.g., Q or N). Such conservative substitutions can further include conservative substitutions with similar non-natural amino acids. Some additional conservative amino acid substitutions include: arginine and homoarginine; methionine and homocysteine; proline and proline analogues having a 4-, 6-, or 7-membered ring; leucine and norleucine; tryptophan and naphthylalanine; phenylalanine and homophenylalanine; and valine and isovaline.

Percent homology as used herein with respect to peptides is found if the two polypeptides or designated segments thereof, when optimally aligned with appropriate amino acid insertions or deletions, are identical in at least about 50% of the amino acids. "Substantial sequence identity" in the polypeptide context means that the amino acids, when compared, are identical when optimally aligned with appropriate amino acid insertions or deletions, in at least about 60% of the amino acids, usually at least about 70%, more usually at least about 80%, preferably at least about 81%, preferably at least about 82%, preferably at least about 83%, preferably at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, more preferably at least about 95%, more preferably at least about 96%, more preferably at least about 97%, more preferably at least about 98%, more preferably at least about 99%, more preferably at least about 99.5%, and more preferably at least about 99.8% of the amino acids.

The determination of sequence identity between two sequences (e.g., between a native sequence and a functional analog) can be accomplished using any alignment tool, including Tatusova et al., Blast 2 sequences—a new tool for comparing protein and nucleotide sequences, *FEMS Microbiol Lett.* 174: 247-250 (1999). Such functional analogs may further comprise additional chemical modifications, such as those known in the art.

"Treat" as used herein refers to any type of treatment that imparts a benefit to a subject, particularly preventing, ameliorating, delaying or retarding the onset or progression of an infection or improving, reducing or curing an infection.

"Concurrently" as used herein means sufficiently close in time to produce a combined effect (that is, concurrently may be simultaneously, or it may be two or more events occurring anytime within the period where the effect of the first compound is still present).

"Pharmaceutically acceptable" as used herein means that the compound or composition is suitable for administration to a subject to achieve the treatments described herein, without unduly deleterious side effects in light of the severity of the disease and necessity of the treatment.

Screening Methods.

This disclosure features, inter alia, methods of screening for compounds or biologics that e.g., interfere with tRNA-protein interactions, e.g., $tRNA^{LYS3}$—protein interactions, e.g., interactions of $tRNA^{LYS3}$ with one or more of the peptides, e.g., one or more peptides with a SEQ ID NO:1-20.

Compounds to be Screened. A variety of agents from various sources can be screened in the methods described herein. Agents to be screened can be naturally occurring (e.g., "biologic") or synthetic molecules. Agents to be screened can be also obtained from natural sources, such as, e.g., marine microorganisms, algae, plants, fungi, etc. Alternatively, agent to be screened can be from combinatorial libraries of agents, including peptides or small molecules, or from existing repertories of chemical compounds synthesized in industry, e.g., by the chemical, pharmaceutical, environmental, agricultural, marine, cosmeceutical, drug, and biotechnological industries. Agents can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, chimeric molecules, etc. (see, e.g., U.S. Pat. No. 7,041,276).

Compound libraries or combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in Affymax, WO 95/12608, Affymax WO 93/06121, Columbia University, WO 94/08051, Pharmacopeia, WO 95/35503 and Scripps, WO 95/30642 (each of which is incorporated herein by reference in its entirety for all purposes). Peptide libraries can also be generated by phage display methods. See, e.g., Devlin, WO 91/18980. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like.

Assay one. As noted above, the present disclosure features, e.g., a method of screening for a compound or biologic for treatment of a retroviral infection, comprising: contacting a $tRNA^{LYS3}$ with at least one peptide that interacts with $tRNA^{LYS3}$; contacting the $RNA^{LYS3}$ and the at least one peptide with one or more candidate compounds; and identifying the one or more candidate compounds that inhibit the interaction of $tRNA^{LYS3}$ with the at least one peptide.

In some embodiments of the foregoing, contacting $tRNA^{LYS3}$ and the at least one peptide with one or more compounds occurs in vitro.

In some embodiments of the foregoing, $tRNA^{LYS3}$ and the at least one peptide are capable of binding.

In some embodiments of the foregoing, the one or more candidate compounds inhibit the binding of $tRNA^{LYS3}$ with the at least one peptide.

In some embodiments of the foregoing, the $tRNA^{LYS3}$ is an anticodon stem loop domain of $tRNA^{LYS3}$.

In some embodiments of the foregoing, the anticodon stem loop domain of $tRNA^{LYS3}$ contains one or more modified nucleoside bases.

In some embodiments of the foregoing, the anticodon stem loop domain of $tRNA^{LYS3}$ contains two modified nucleoside bases.

In some embodiments of the foregoing, the anticodon stem loop domain of $tRNA^{LYS3}$ contains a 5-methoxymethyl-2-thiouridine at position 34 and a 2-methylthio-N-6-threonyl-carbamoyladenosine at position 37.

In some embodiments of the foregoing, the at least one peptide is capable of recruiting $tRNA^{LYS3}$ for viral replication.

In some embodiments of the foregoing, the at least one peptide interferes with the ability of a viral protein to recruit $tRNA^{LYS3}$ in viral reverse transcription.

In some embodiments of the foregoing, the at least one peptide interferes with the ability of a host protein to assist in the recruitment of $tRNA^{LYS3}$ in viral reverse transcription.

In some embodiments of the foregoing, the at least one peptide is capable of interfering with the ability of $tRNA^{LYS3}$ to prime reverse transcription in vivo or in vitro.

In some embodiments of the foregoing, the at least one peptide inhibits $tRNA^{LYS3}$ annealing or priming on a viral genome thereby reducing viral replication.

In some embodiments of the foregoing, the at least one peptide binds to an anticodon stem loop structure of $tRNA^{LYS3}$.

In some embodiments of the foregoing, the at least one peptide prevents the viral protein from binding to an anticodon stem loop domain of the $tRNA^{LYS3}$.

In some embodiments of the foregoing, the at least one peptide is a mimetic peptide. In some embodiments of the foregoing, the mimetic peptide mimics a protein that binds to $tRNA^{LYS3}$ in a viral infection.

In some embodiments of the foregoing, the mimetic peptide is a viral protein mimetic peptide.

In some embodiments of the foregoing, the mimetic peptide mimics a protein selected from the group of viral proteins consisting of HIV polyprotein, reverse transcriptase, nucleocapsid protein, gag protein, protease, integrase, env protein, p24, gp41, gp120, gp140, gp160, rev, nef and pol.

In some embodiments of the foregoing, the mimetic peptide is a host protein mimetic peptide.

In some embodiments of the foregoing, the mimetic peptide is a host lysyl-tRNA mimetic protein.

In some embodiments of the foregoing, the at least one peptide is an active peptide as described above.

In some embodiments of the foregoing, the at least one peptide is labelled (e.g., with a fluorescent, enzyme, or isotope label).

In some embodiments of the foregoing, the method further comprises detecting fluorescence after contacting the $tRNA^{LYS3}$ and the at least one peptide with one or more candidate compounds, wherein a change in fluorescence is indicative of a compound or biologic that binds the $tRNA^{LYS3}$ and/or the at least one peptide.

In some embodiments of the foregoing, the method further comprises detecting fluorescence after contacting the $tRNA^{LYS3}$ and the at least one peptide with one or more candidate compounds, wherein a change in fluorescence is indicative of a compound or biologic that inhibits the binding of the $tRNA^{LYS3}$ and the at least one peptide.

In some embodiments of the foregoing, a change in fluorescence is indicative of a compound or biologic effective for the treatment or prevention of a retroviral infection.

In some embodiments of the foregoing, the at least one peptide is labeled with biotin. The at least one biotin-labeled peptide can be bound to a solid support coated with avidin.

Assay Two. The present disclosure further provides a method of, e.g., screening for a therapeutic compound or biologic for treatment of a retroviral infection, comprising: contacting a $tRNA^{LYS3}$ with one or more compounds and at least one reporter peptide; and identifying compounds that bind to $tRNA^{LYS3}$.

In some embodiments of the foregoing, the $tRNA^{LYS3}$ that contacts the one or more compounds is a $tRNA^{LYS3}$ anticodon stem loop domain.

In some embodiments of the foregoing, the anticodon stem loop domain of $tRNA^{LYS3}$ contains one or more modified nucleoside bases.

In some embodiments of the foregoing, the anticodon stem loop domain of $tRNA^{LYS3}$ contains two modified nucleoside bases.

In some embodiments of the foregoing, the anticodon stem loop domain of $tRNA^{LYS3}$ contains a 5-methoxymethyl-2-thiouridine at position 34 and a 2-methylthio-N-6-threonyl-carbamoyladenosine at position 37.

In some embodiments of the foregoing, the $tRNA^{LYS3}$ anticodon stem loop domain is a human $tRNA^{LYS3}$ anticodon stem loop domain.

In some embodiments of the foregoing, the reporter peptide comprises a detection moiety (e.g., a fluorescence moiety).

In some embodiments of the foregoing, the reporter peptide is capable of interacting with the $tRNA^{LYS3}$ in the absence of the one or more compounds.

In some embodiments of the foregoing, the fluorescence moiety fluoresces differently when the reporter peptide interacts with the $tRNA^{LYS3}$ compared to when the reporter peptide does not interact with the $tRNA^{LYS3}$.

In some embodiments of the foregoing, the reporter peptide is capable of binding with the $tRNA^{LYS3}$ in the absence of the one or more compounds.

In some embodiments of the foregoing, the fluorescence moiety fluoresces differently when the reporter peptide binds to the $tRNA^{LYS3}$ compared to when the reporter peptide does not bind to the $tRNA^{LYS3}$.

In some embodiments of the foregoing, the reporter peptide is a mimetic peptide.

In some embodiments of the foregoing, the mimetic peptide mimics a protein that binds to $tRNA^{LYS3}$ in a viral infection.

In some embodiments of the foregoing, the mimetic peptide is a viral protein mimetic peptide.

In some embodiments of the foregoing, the mimetic peptide mimics a protein selected from the group of viral proteins consisting of HIV polyprotein, reverse transcriptase, nucleocapsid protein, gag protein, protease, integrase, env protein, p24, gp41, gp120, gp140, gp160, rev, nef and pol.

In some embodiments of the foregoing, the mimetic peptide is a host protein mimetic peptide.

In some embodiments of the foregoing, the mimetic peptide is a host lysyl-tRNA mimetic protein.

In some embodiments of the foregoing, the reporter peptide comprises a peptide active agent as described herein above.

In some embodiments of the foregoing, the at least one reporter peptide is two or more reporter peptides, each reporter peptide with a different detection moiety.

Therapeutic Compositions.

The present disclosure also features a therapeutic composition for treatment or prevention of a retroviral infection comprising at least one peptide that interferes with the ability of a protein, nucleic acid or metabolite to recruit host $tRNA^{LYS3}$ for reverse transcription and a pharmaceutically acceptable carrier, diluent or excipient.

In some embodiments of the foregoing, the protein, nucleic acid or metabolite is a retroviral protein, nucleic acid, metabolite or a fragment or subunit thereof.

In some embodiments of the foregoing, the retroviral protein is selected from the group of proteins consisting of HIV polyprotein, reverse transcriptase, nucleocapsid protein, gag protein, protease, integrase, env protein, p24, gp41, gp120, gp140, gp160, rev, nef, and pol.

In some embodiments of the foregoing, retroviral nucleic acid is a nucleic acid encoding a retroviral protein selected from the group of proteins consisting of HIV polyprotein, reverse transcriptase, nucleocapsid protein, gag protein, protease, integrase, env protein, p24, gp41, gp120, gp140, gp160, rev, nef, and pol.

In some embodiments of the foregoing, said retroviral protein, nucleic acid, metabolite or a fragment or subunit thereof is a lentivirus protein, nucleic acid, metabolite or a fragment or subunit thereof.

In some embodiments of the foregoing, said lentivirus protein, nucleic acid, metabolite or a fragment or subunit thereof is an HIV protein, nucleic acid, metabolite or a fragment or subunit thereof.

In some embodiments of the foregoing, said protein, nucleic acid or metabolite is a host protein, nucleic acid, metabolite or a fragment or subunit thereof.

In some embodiments of the foregoing, the host is a mammal. In some embodiments of the foregoing, said host is a human.

In some embodiments of the foregoing, said host protein is lysyl-tRNA synthetase.

In some embodiments of the foregoing, said at least one peptide is a heterologous peptide.

In some embodiments of the foregoing, said peptide binds to an anticodon stem loop structure of $tRNA^{LYS3}$.

In some embodiments of the foregoing, said peptide prevents the protein, nucleic acid or metabolite from binding to an anticodon stem loop domain of the $tRNA^{LYS3}$.

Such compositions can be used in methods of treatment as further described below.

Peptide Active Agents.

As noted above, the present disclosure provides a peptide (sometimes also referred to as an "active compound" herein) comprising, consisting of or consisting essentially of one or more amino acid sequences selected from: (a) the peptides set forth in Table 1 herein; (b) a fragment (e.g., of 10 or more contiguous amino acids) from an amino acid sequence of Table 1 herein; and (c) an amino acid sequence that is homologous (e.g., at least about 90% homologous) to an amino acid sequence of Table 1 herein. Such peptides may be in the form of pharmaceutically acceptable salts.

In some embodiments of the foregoing, the fragment of 10 or more contiguous amino acids is functionally equivalent to the corresponding amino acid sequence of SEQ ID NO.: 1-20 (e.g., interferes with or is capable of interfering with the ability of a virus to use host $tRNA^{LYS3}$ to prime reverse transcription).

In some embodiments of the foregoing, the homologous amino acid sequence is functionally equivalent to the corresponding amino acid sequence of SEQ ID NO.: 1-20 (e.g., interferes with or is capable of interfering with the ability of a virus to use host $tRNA^{LYS3}$ to prime reverse transcription).

In some embodiments of the foregoing, the peptide is at least about 10 amino acids in length, 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length.

In some embodiments of the foregoing, the peptide is less than about 12 amino acids in length, less than about 15 amino acids in length, less than about 20 amino acids in length, less than about 25 amino acids in length, less than about 30 amino acids in length, less than about 35 amino acids in length, less than about 40 amino acids in length, less than about 50 amino acids in length, less than about 60 amino acids in length, less than about 70 amino acids in length, less than about 80 amino acids in length, less than about 90 amino acids in length, less than about 100 amino acids in length, or less than about 150 amino acids in length.

In some embodiments of the foregoing, the peptide contains an amino acid analog or derivative.

In some embodiments of the foregoing, the homologous amino acid sequence is at least about 95% or 99% homologous to an amino acid sequence from the group of amino acid sequences consisting of SEQ ID NOs.: 1-20.

In some embodiments of the foregoing, the peptide is modified to exhibit increased serum half life compared to an unmodified peptide.

In some embodiments of the foregoing, the peptide is, comprises, consists of or consists essentially of D-amino acid(s).

In some embodiments of the foregoing, the peptide is interferes with or is capable of interfering with the ability of a virus to use host $tRNA^{LYS3}$ to prime reverse transcription.

In some embodiments of the foregoing, the peptide peptide interferes with or is capable of interfering with the ability of a host protein to assist in the recruitment of $tRNA^{LYS3}$ in viral reverse transcription.

In some embodiments of the foregoing, the peptide inhibits $tRNA^{LYS3}$ annealing or priming on a viral genome thereby reducing viral replication.

In some embodiments of the foregoing, the peptide binds to an anticodon stem loop structure of $tRNA^{LYS3}$.

In some embodiments of the foregoing, the peptide prevents the viral protein from binding to an anticodon stem loop domain of the $tRNA^{LYS3}$.

In some embodiments of the foregoing, the peptide is isolated and/or purified.

In some embodiments of the foregoing, the peptide is effective as a prophylactic for treatment of a retroviral infection in a subject.

In some embodiments of the foregoing, the peptide is effective for the prevention of a retroviral infection in a subject.

Peptide active agents of the present invention can be produced by synthetic chemical techniques, by recombinant or molecular biology techniques, or combinations thereof, that will be readily apparent to those skilled in the art. See, e.g., U.S. Pat. Nos. 7,265,084; 7,144,720; 6,989,146; 5,436,137; and 4,831,119. Hence, the present invention further provides a fusprotein comprising the peptide active agents described herein, nucleic acids encoding such fusion proteins or the peptide active agents described herein, vectors comprising such nucleic acid and host cells containing the same.

Pharmaceutically acceptable salts. The peptide active compounds disclosed herein can, as noted above, be prepared in the form of their pharmaceutically acceptable salts, hydrates and solvates. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Peptide modification. The peptides featured herein, e.g., peptides with SEQ ID NOs.:1-20, can also be modified, e.g., to extend their half-life. The peptides can also be modified to allow for their easier entry into a cell, e.g., modified with a lipophilic moiety or an active peptide transporter substrate (see, e.g., Aurora, Proteomics, Business Briefing; Future Drug Discovery 2006, pages 38-40). Modifications can also include conjugation to detection moieties, e.g., labels, e.g., fluorescent labels, that can be useful in, e.g., certain screening assays. Peptide modification methods are known in the art.

In one embodiment, the peptides can be N-acetylated and/ or C-amidated to protect them from degradation and/or make them mimic more closely the charges of the alpha amino and carboxyl groups in the native protein.

The peptides can also be modified by addition of polyethylene glycol (PEG) polymer chains. PEGylation can, e.g., cause the peptides to become more water soluble and/or protect the peptide bonds from hydrolysis.

Other N-terminal modifications can include, e.g., addition of benzyloxycarbonyl, biotin, dabcyl, dabsyl, dansyl, dinitrophenyl, fluorescein, FMOC, lissamine rhodamine, 7-methoxycoumarin acetic acid, N-methyl, myristoylation, palmitoylation, steroylation, formylation, and cinnamoylation. Other C-terminal modifications can include addition of 4-branch MAP resin.

Such peptide active compounds can be used in the methods of treatment further described below.

Pharmaceutical Formulations and Methods of Administration.

The peptide active compounds featured herein may be formulated, e.g., into therapeutic compositions, with conventional carriers, diluents and excipients, which will be selected in accord with ordinary practice (see, e.g., Remington's Pharmaceutical Sciences, 18th Ed., Mack Publishing Co. (1990); see also Cai et al., US Patent Application US 2007/0072831). Tablets will contain excipients, glidants, fillers, binders, diluents and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Featured compounds and their physiologically acceptable salts (hereafter collectively referred to as the active ingredients) may be administered by any route appropriate to the condition to be treated, suitable routes including, e.g., oral, rectal, nasal, topical (including ocular, buccal and sublingual), vaginal and parenteral (including subcutaneous, intramuscular, intravenous, intradermal, intrathecal and epidural). The preferred route of administration may vary with, for example, the condition of the recipient.

While it is possible for the active ingredients to be administered alone, it is preferable to present them as pharmaceutical formulations. The formulations, both for veterinary and for human use, disclosed herein comprise at least one active ingredient, as above defined, together with one or more pharmaceutically acceptable carriers (excipients, diluents, etc.) thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include, e.g., the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations disclosed herein suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of the compositions featured herein may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the disclosed formulations include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations featured herein may include other agents conventional in the art having regard to the type of formulation in question, for example those suitable for oral administration may include flavoring agents.

Dosage will depend upon the route of administration, particular formulation, condition of the subject, etc., and can be determined in accordance with known techniques. In one embodiment, for subcutaneous injection, the dosage may be from 20 or 50 mg up to 100 or 100 mg of the peptide active agent, once or twice per day.

In some embodiments of the foregoing, the administration of said therapeutic composition or peptide active compound reduces viral load in said subject by at least about 5%, at least about 10%, at least about 20%, at least about 30%, at least about 40%, at least about 50%, at least about 60%, at least about 70%, at least about 80%, at least about 90%, or about 99%.

In some embodiments of the foregoing, the administration of therapeutic composition or peptide active compound increases CD4 levels by at least about 5%, at least about 10%, at least about 20%, at least about 30%, at least about 40%, at least about 50%, at least about 60%, at least about 70%, at least about 80%, at least about 90%, or about 100%.

The methods disclosed herein may be carried out with the described active compounds, e.g., peptides of SEQ ID NOs: 1-20 alone, or in combination with or concurrently with the administration of one or more other active antiviral compounds as discussed below.

Likewise, presently featured compositions may contain active agents/peptides as described above as a single antiviral agent, or may further include one or more additional active antiviral compounds as discussed below.

Combination and Conjugation Compositions and Methods.

Additional anti-viral active agents that may be used in carrying out the methods and compositions described herein include, e.g., entry inhibitors, HIV-protease inhibitors, nucleoside reverse transcriptase inhibitors, non-nucleoside reverse transcriptase inhibitors, integrase inhibitors, and combinations thereof. These and other active agents can be used in combination with the peptides and compositions featured herein. They can also be conjugated to the disclosed peptides and compositions.

Numerous examples of such additional antiviral active agents are known and described in, for Example, US Patent Application Publication No. 2006/0234982 to Dahl et al. at Table A therein, and include but are not limited to: 5,6 dihydro-5-azacytidine 5-aza 2' deoxycytidine 5-azacytidine 5-yl-carbocyclic 2'-deoxyguanosine (BMS200,475) 9 (arabinofuranosyl)guanine; 9-(2' deoxyribofuranosyl)guanine 9-(2'-deoxy 2' fluororibofuranosyl)-2,6-diaminopurine 9-(2'-deoxy 2' fluororibofuranosyl)guanine 9-(2'-deoxyribofuranosyl)-2,6 diaminopurine 9-(arabinofuranosyl)-2,6 diaminopurine Abacavir, Ziagen™ Acyclovir, ACV; 9-(2-hydroxyethoxylmethyl)guanine Adefovir dipivoxil, Hepsera™ amdoxivir, DAPD Amprenavir, Agenerase™ araA; 9-beta-D-arabinofuranosyladenine (Vidarabine) atazanivir sulfate (Reyataz™) AZT; 3'-azido-2',3'-dideoxythymdine, Zidovudine, (Retrovir™) BHCG; (.+-.)-(1a,2b,3a)-9-[2,3-bis(hydroxymethyl)cyclobutyl]guanine BMS200,475; 5-yl-carbocyclic 2'-deoxyguanosine Buciclovir; (R) 9-(3,4-dihydroxybutyl)guanine BvaraU; 1-beta-D-arabinofuranosyl-E-5-(2-bromovinyl)uracil (Sorivudine) Calanolide A Capravirine CDG; carbocyclic 2'-deoxyguanosine Cidofovir, HPMPC; (S)-9-(3-hydroxy-2-phosphonylmethoxypropyl)cytosine Clevudine, L-FMAU; 2'-Fluoro-5-methyl-beta-L-arabino-furanosyluracil Combivir™ (lamivudine/zidovudine) Cytallene; [1-(4'-hydroxy-1',2'-butadienyl)cytosine] d4C; 3'-deoxy-2',3'-didehydrocytidine DAPD; (−)-beta-D-2,6-diaminopurine dioxolane ddA; 2',3'-dideoxyadenosine ddAPR; 2,6-diaminopurine-2',3'-dideoxyriboside ddC; 2',3'-dideoxycytidine (Zalcitabine) ddI; 2',3'-dideoxyinosine, didanosine, (Videx™, Videx™ EC) Delavirdine, Rescriptor™ Didanosine, ddI, Videx™ 2',3'-dideoxyinosine DXG; dioxolane guanosine E-5-(2-bromovinyl)-2'-deoxyuridine Efavirenz, Sustiva™ Enfuvirtide, Fuzeon™ F-ara-A; fluoroarabinosyladenosine (Fludarabine) FDOC; (−)-beta-D-5-fluoro-1-[2-(hydroxymethyl)-1,3-dioxolane]cytosine FEAU; 2'-deoxy-2'-fluoro-1-beta-D-arabinofuranosyl-5-ethyluracil FIAC; 1-(2-deoxy-2-fluoro-beta-D-arabinofuranosyl)-5-iodocytosine FIAU; 1-(2-deoxy-2-fluoro-beta-D-arabinofuranosyl)-5-iodouridine FLG; 2',3'-dideoxy-3'-fluoroguanosine FLT; 3'-deoxy-3'-fluorothymidine Fludarabine; F-ara-A; fluoroarabinosyladenosine FMAU; 2'-Fluoro-5-methyl-beta-L-arabino-furanosyluracil FMdC Foscarnet; phosphonoformic acid, PFA FPMPA; 9-(3-fluoro-2-phosphonylmethoxypropyl)adenine Gancyclovir, GCV; 9-(1,3-dihydroxy-2-propoxymethyl)guanine GS-7340; 9-[R-2-[[(S)-[[(S)-1-(isopropoxycarbonyl)ethyl]amino]-phenoxyphosphinypl methoxy]propyl]adenine HPMPA; (S)-9-(3-hydroxy-2-phosphonylmethoxypropyl)adenine HPMPC; (S)-9-(3-hydroxy-2-phosphonylmethoxypropyl)cytosine (Cidofovir) Hydroxyurea, Droxia™ Indinavir, Crixivan™ Kaletra™. (lopinavir/ritonavir) Lamivudine, 3TC, Epivir™; (2R,5S, cis)-4-amino-1-(2-hydroxymethyl-1,3-oxathiolan-5-yl)-(1H)-pyrimidin-2-one L-d4C; L-3'-deoxy-2',3'-didehydrocytidine L-ddC; L-2',3'-dideoxycytidine L-Fd4C; L-3'-deoxy-2',3'-didehydro-5-fluorocytidine L-FddC; L-2',3'-dideoxy-5-fluorocytidine Lopinavir Nelfinavir, Viracept™ Nevirapine, Viramune™ Oxetanocin A; 9-(2-deoxy-2-hydroxymethyl-beta-D-erythro-oxetanosyl)adenine Oxetanocin G; 9-(2-deoxy-2-hydroxymethyl-beta-D-erythro-oxetanosyl)guanine Penciclovir PMEDAP; 9-(2-phosphonylmethoxyethyl)-2,6-diaminopurine PMPA, tenofovir; (R)-9-(2-phosphonylmethoxypropyl)adenine PPA; phosphonoacetic acid Ribavirin; 1-beta-D-ribofuranosyl-1,2,4-triazole-3-carboxamide Ritonavir, Norvir™ Saquinavir, Invirase™, Fortovase™ Sorivudine, BvaraU; 1-beta-D-arabinofuranosyl-E-5-(2-bromovinyl)uracil Stavudine, d4T, Zerit™; 2',3'-didehydro-3'-deoxythymidine Trifluorothymidine, TFT; Trifluorothymidine Trizivir™ (abacavir sulfate/lamivudine/zidovudine) Vidarabine, araA; 9-beta-D-arabinofuranosyladenine Viread™, tenofovir disoproxil fumarate (DF), Bis POC PMPA, TDF; 2,4,6,8-Tetraoxa-5-phosphanonanedioic acid, 5-[[(1R)-2-(6-amino-9H-purin-9-yl)-1-methylethoxy]methyl]-, bis(1-methylethyl) ester, 5-oxide, (2E)-2-butenedioate (1:1) Zalcitabine, Hivid™, ddC; 2',3'-dideoxycytidine Zidovudine, AZT, Retrovir™; 3'-azido-2',3'-dideoxythymdine Zonavir; 5-propynyl-1-arabinosyluracil.

Example 1

Selection of Compounds

The functional interactions of human tRNA$^{LYS3}$ (htRNA$^{LYS3}$) generally precede and promote the replication of HIV. The tRNA's role is as a primer of reverse transcriptase. Thus, the interactions of the tRNA with viral proteins prior to replication are validated targets of intervention. htRNA$^{LYS3}$ is recruited by HIV proteins to be annealed to the HIV genome and, in subsequent infections, to act as primer of HIV reverse transcriptase. One of the three human transfer RNAs specific for the amino acid lysine, tRNA$^{LYS3}$, is used to prime the replication of HIV upon the infection of a cell. The human tRNA$^{LYS3}$ is recruited by HIV proteins into the new viral capsids. When these viruses are released, and find and infect new cells, the captured tRNA$^{LYS3}$ participates in the reverse transcription of the viral genome. All lentiviruses, such as HIV, are so dedicated to tRNA$^{LYS3}$ that mutation in the viral genome to complement a human tRNA only transiently changes the primer. During continued culturing of the virus, it reverts to tRNA$^{LYS3}$ as primer. Human isolates of HIV, no matter what serotype or subspecies, use tRNA$^{LYS3}$. Even if the viral genome is mutated in more than one location in order for the virus to use another human tRNA for priming reverse transcription, tRNA$^{LYS3}$ is still greatly accumulated in the viral capsid by HIV proteins that recruit it from the host cell cytoplasm. The proteins that recruit tRNA$^{LYS3}$ have not been specifically identified. Without being limited by theory, it is thought that the HIV polyprotein composed of the reverse transcriptase, nucleocapsid protein, and gag protein is involved. The human lysyl-tRNA synthetase may also be recruited by HIV to help in the trafficking of the tRNA into the capsid. The nucleocapsid protein is known to be active in the relaxing, denaturing of both the human tRNA$^{LYS3}$ and the viral genome for purposes of annealing the tRNA to the genome. We chose to find peptides that would mimic one or more of these HIV proteins in their recognition and binding to human tRNA$^{LYS3}$.

Figure 2:
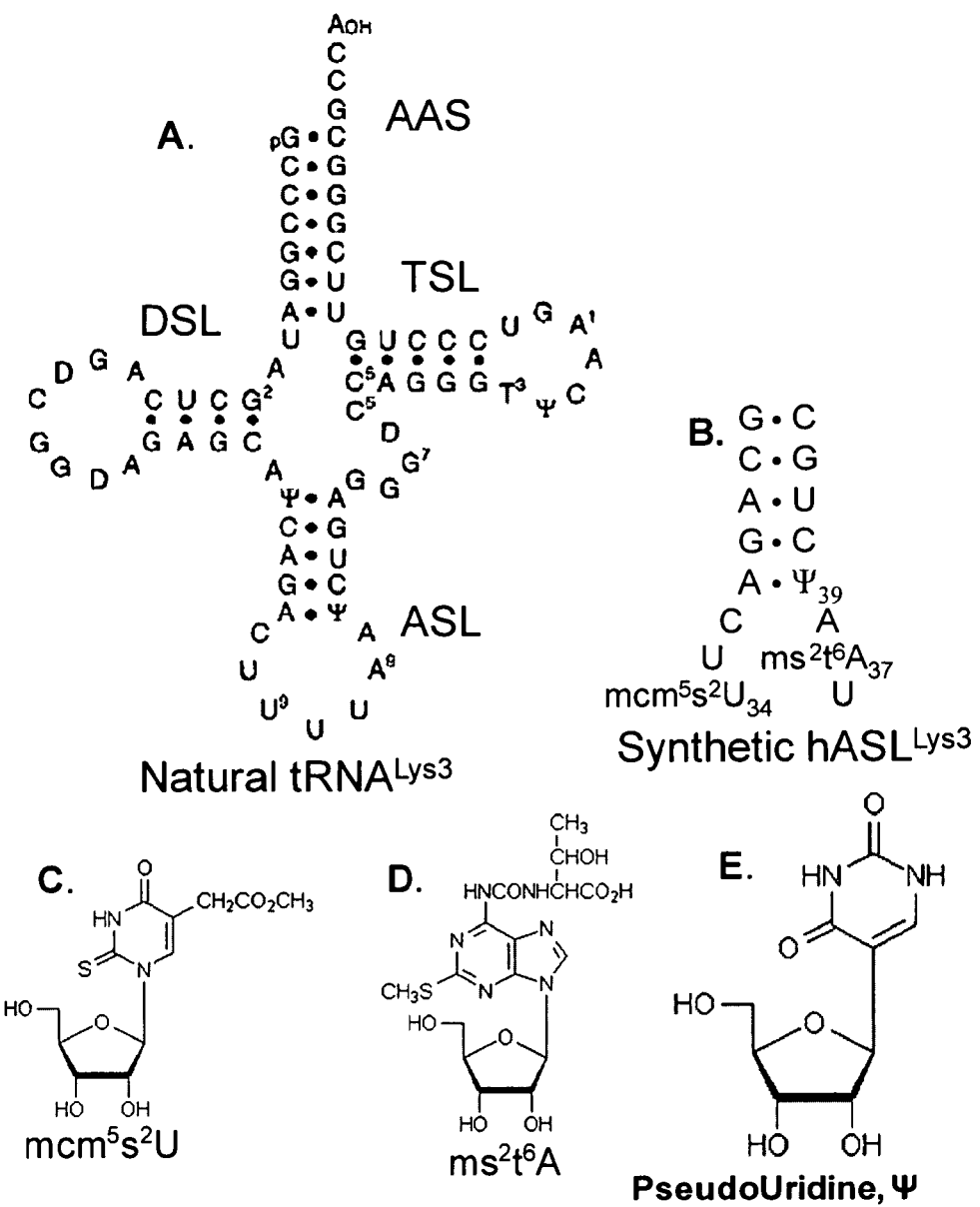
FIG. 2: A. Sequence and secondary structure of Human tRNA$^{LYS3}$ (SEQ ID NO:21). AAS=amino accepting stem; DSL=dihydrouridine stem and loop; TSL=Thymidine stem and loop; ASL=anticodon stem and loop. G$^2$=N2-methylguanosine; Ψ=pseudoUridine (pictured in E); U⁹=5-methyoxymethyl-2-thiouridine (pictured in C); A⁶=2-methyl-thio-N6-threonylcarbamoyladenosine (pictured in D); G⁷=N7-methylguanosine; T=ribothymidine; A1=N1-methyladenosine. B. Synthetic anticodon stem and loop of human tRNA$^{LYS3}$ (hASL$^{LYS3}$, SEQ ID NO:22). A G-C base pair was substituted for the natural first base pair of the stem, an A-U to promote stability in this model target.
Figure 3:
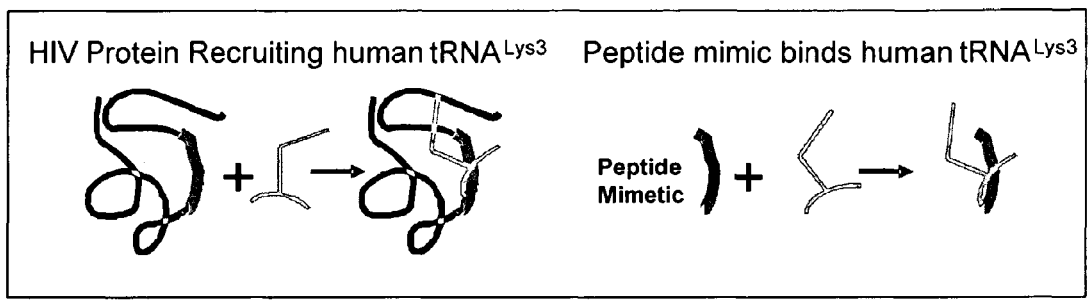
FIG. 3: Utilizing peptides as tools to screen for small molecules that inhibit recruitment of tRNA$^{LYS3}$. A. Recruitment of human tRNA$^{LYS3}$ by a viral protein, and the peptide as a mimetic. B. Fluorescent peptide as a reporter in an assay that assesses the interference of a small molecule with the binding of tRNA$^{LYS3}$ by the peptide. Left: Fluoroescence quenched by binding of tRNA. Right: Fluorescence uneffected in presence of interfering small molecule that could bind either the tRNA of the peptide.
Figure 3:
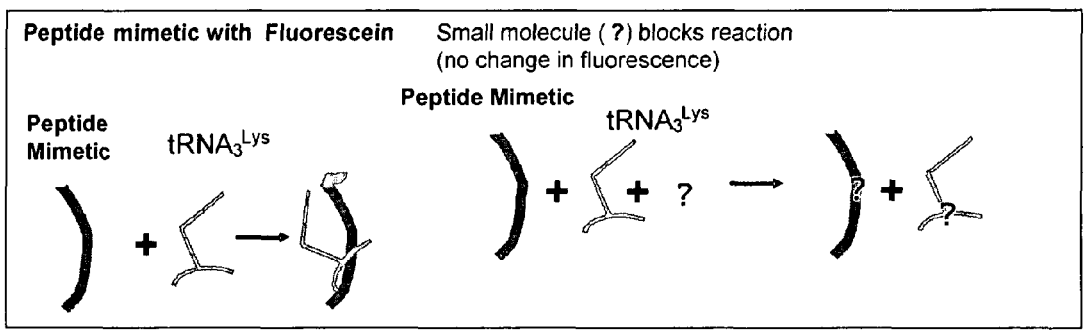

The human cell has some 40 different tRNAs that are used to translate the genetic code into proteins. Cytoplasmic tRNAs have conserved sequences, a conserved two dimensional cloverleaf structure and a conserved three dimensional L-shaped structure. Yet tRNA$^{LYS3}$ is distinguished by the HIV proteins. tRNA$^{LYS3}$ and its two isoaccepting lysine tRNAs 1 and 2 species are recognized and aminoacylated by the one human lysyl-tRNA synthetase. Yet, HIV protein differentiate tRNA$^{LYS3}$ from lysine tRNAs 1 and 2 (FIG. 1). There are two nucleotide sequences that distinguish tRNA$^{LYS3}$ (FIG. 2A) from tRNA$^{LYS\ 1,2}$. The first is the 3'-terminal sequence of 18 nucleotides that complement the primer binding site (PBS) of the HIV genome. However, almost all of these nucleosides, A, C, G and U, are within the double stranded helical segments of the tRNA, the amino acid accepting-stem and the T-stem. However, the second distinguishing sequence is that of the tRNA$^{LYS3}$ anticodon stem and loop domain, hASL$^{LYS3}$ (FIG. 2B). This sequence is composed of five base pairs and a seven member loop, the latter of which has seven unpaired nucleosides available for protein and peptide recognition and binding. In fact, these nucleosides are recognition determinants for the human lysyl-tRNA synthetase. The hASL$^{LYS3}$ has two modified nucleosides, the chemistries of which in combination are unique to tRNA$^{LYS3}$. That is, though other human tRNAs may have parts of these chemical modifications, these tRNAs do not have the identical combination. At the anticodon wobble position 34, hASL$^{LYS3}$ has a 5-methoxymethyl-2-thiouridine, mcm$^5$s$^2$U$_{34}$ (FIG. 2C) and at position 37, just 3'- to the anticodon a 2-methylthio-N-6-threonylcarbamoyladenosine, ms$^2$t$^6$A$_{37}$ (FIG. 2D).

Twenty peptides have been selected from huge libraries of sequences (~10$^{15}$) for their abilities to bind hASL$^{LYS3}$. Each of the peptides is small, 15 or 16 amino acids in length. Peptides were obtained by phage display library screening of the hASL$^{LYS3}$ with native modifications. The methodology is that of Agris et al, *Journal of Protein Chemistry* 18, 425-435 (1999) and Eshete et al., *The Protein Journal* 26, 61 73 (2007). The libraries included a random 15 mer library, as well as a library with two cysteines and 14 other random positions. The hASL$^{LYS3}$ has been chemically synthesized (Sundaram et al. *J. Org. Chem.* 2000; Bajji and Davis, *Org. Lett.* 2000; Bajji and Davis, *J. Org. Chem.* 2002).

Some years ago, the idea was advanced that peptides can be selected to bind to specific RNA sequences and structures, and in particular to those sequences and structures that contain naturally modified nucleosides (posttranscriptional modifications) (see, e.g., P. Mucha et al., *biochemistry* 40, 14191-14199 (2001); P. Mucha et al., RNA 8, 698-704 (2002); P. Mucha et al., *The Protein Journal* 23, 33-38 (2004).

One such peptide selected against yeast ASL$^{Phe}$ recognized and bound the native tRNA, and in doing so inhibited aminoacylation of the tRNA by the yeast phenylalanyl-tRNA synthetase (Mucha et al. Biochemistry).

Peptides that mimic the recognition of hASL$^{LYS3}$ by HIV proteins can be used as tools to select even smaller molecules, organic compounds, from huge combinatorial libraries, as candidate therapeutics that interfere with the peptides' recognition of the RNA. The best of these small molecule candidate therapeutics would interfere with the natural function of the RNA. The peptides may have sufficient value in binding the RNA as to significantly interfere with the RNA function that they themselves could be therapeutics.

The peptides that specifically bind to hASL$^{LYS3}$ are:

1) Tools for the purposes of selecting small molecule candidate therapeutics that would interfere with HIV recognition and recruitment of tRNA$^{LYS3}$ as primer of reverse transcription;

2) Therapeutic agents themselves as inhibitors of the recruitment of tRNA$^{LYS3}$ by HIV or other lentivirus proteins as primer of reverse transcription, and 3) Models for peptides that interfere with other RNA/protein interactions that are validated targets of intervention in human disease.

The specific amino acid sequences of the twenty peptides that bind hASL$^{LYS3}$ are set forth in Table 1 below.

TABLE 1

| Phage Display Library Selected Peptides | Calculated Molecular Weights |
|---|---|
| 15 mers | |
| FSVSFPSLPAPPDRS (SEQ ID NO: 1) | 1,603.8 |
| GRVTYYSCGVSLLFQ (SEQ ID NO: 2) | 1,693.0 |
| AGPVPLHSLSYYYNQ (SEQ ID NO: 3) | 1,708.9 |
| RAVMTVVWPVSFAGF (SEQ ID NO: 4) | 1,667.0 |
| RVTHHAFLGAHRTVG (SEQ ID NO: 5) | 1,658.9 |
| PAVASTSSLIIDGPF (SEQ ID NO: 6) | 1,474.7 |
| PKAFQYGGRAVGGLW (SEQ ID NO: 7) | 1,606.9 |
| AAHVSEHYVSGSLRP (SEQ ID NO: 8) | 1,609.8 |
| ASVGPAPWAMTPPVS (SEQ ID NO: 9) | 1,467.7 |
| APALWYPWRSLLPLY (SEQ ID NO: 10) | 1,846.2 |
| ASLHPVPKTWFFLLS (SEQ ID NO: 11) | 1,743.1 |
| WSHSRNTADVPVSML (SEQ ID NO: 12) | 1,699.9 |
| 16 mers | |
| HRGYCRDRVVNCGEYF (SEQ ID NO: 13) | 1,974.2 |
| PHRQCSAPAKSCKILP (SEQ ID NO: 14) | 1,736.1 |
| TLPACHELPKHCKRRG (SEQ ID NO: 15) | 1,846.2 |
| TLPACHELPKHCNEAR (SEQ ID NO: 16) | 1,819.1 |
| NGPECNAYMVRCRGYH (SEQ ID NO: 17) | 1,870.1 |
| GNSNCPMLNEQCPWQD (SEQ ID NO: 18) | 1,836.0 |

TABLE 1-continued

| Phage Display Library Selected Peptides | Calculated Molecular Weights |
|---|---|
| HTETCINIRNTCTTVA (SEQ ID NO: 19) | 1,777.0 |
| LKLPCKITINNCQLAG (SEQ ID NO: 20) | 1,729.2 |

Example 2

Biological Activity

FIG. 4 shows the anticodon stem and loop domains (ASL) of the fully modified human tRNA$^{LYS3}$, the primer of HIV reverse transcriptase, and control ASLs of the unmodified ASL$^{LYS3}$ and the unmodified E. coli ASLVal3. The sequences of the target ASLLys3 and that of control ASLs are shown. Peptides were selected against the ASLLys3 and tested against all three. The ASL$^{LYS3}$ contains the natural modified nucleosides, 5-methoxycarbonylmethyl-2-thiouridine-34 (mcm5s2U34), 2-methylthio-N6-threonylcarbamoyladenosine-37 (ms2t6A37), and pseudouridine-39 (Ψ39).

FIG. 5 shows that control peptide does not bind the target modified ASL$^{LYS3}$, nor the control ASLs. Peptides were selected by phage display methods to bind to the modified ASL$^{LYS3}$. Control peptides were selected for their lack of recognition. Each peptide is synthesized with a conjugated fluorescein as a reporter. Here control peptide #21 is titrated with the three ASLs and the fluorescence is monitored.

FIG. 6 shows that experimental and control peptides do not exhibit binding to the unmodified ASL$^{LYS3}$. Peptides #6 and #17 were selected by phage display methods to bind to the modified ASL$^{LYS3}$. These peptides along with control peptide #21 were synthesized with a conjugated fluorescein as a reporter. Here the three peptides are titrated with the unmodified ASL$^{LYS3}$ and the fluorescence is monitored.

FIG. 7 shows that experimental peptides bind to the modified ASL$^{LYS3}$. Peptides #6 and #17 were selected by phage display methods to bind to the modified ASL$^{LYS3}$. These peptides along with control peptide #21 were synthesized with a conjugated fluorescein as a reporter. Here the peptides are titrated with the modified ASLLys3 and the fluorescence is monitored. A comparison of FIG. 7 with FIG. 8 demonstrates that peptides #6 and #7 are specifically recognizing the modifications of the ASLLys3, an important portion of the primer of HIV replication.

FIG. 8 shows feline cells loaded with fluorescein-conjugated peptide #6. Feline (FEA) cells are "shear-loaded" with the peptide #6 that binds the modified ASLLys3. Fluorescein-conjugated, peptide #6 is located with fluorescence microscopy First row: Sham loaded cells. Second row: Peptide loaded. Third row: Peptide loaded at 40× magnification. The peptide is located to the cytoplasm. Toxicity, determined by staining after 1, 2 and 3 days, indicated that the peptide is not toxic at the concentrations used for loading.

FIG. 9 shows that feline cells infected with equine infectious anemia virus (EIAV) and loaded with fluorescein-conjugated peptide #6 have significantly reduced reverse transcriptase activity. EIAV is a lentivirus as is HIV, and as such utilizes the host cell tRNA$^{LYS3}$ for priming reverse transcription. EIAV infected feline (FEA) cells are "shear-loaded" with three concentrations (5, 10, 35) of peptide #6 that binds the modified ASL$^{LYS3}$ portion of HIV primer. Cells are sham loaded with phosphate buffered saline (PBS). The effect of the peptide on reverse transcriptase activity and on toxicity are determined after 1, 2 and 3 days. The peptide #6 exhibits significant bioactivity in cells against HIV reverse transcription at days 2 and 3. Staining of the cells indicated that the peptide was not toxic at the low and middle concentrations and only slightly toxic at high concentration.

The foregoing is illustrative of the present compositions, methods, and uses, and is not to be construed as limiting thereof. The compositions, methods, and uses featured herein are defined by the following claims, with equivalents of the claims to be included therein.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

That which is claimed is:

1. A peptide comprising one or more amino acid sequences selected from:
   (a) RVTHHAFLGAHRTVG (SEQ ID NO: 5);
   (b) a fragment of 10 or more contiguous amino acids from an amino acid sequence of SEQ ID NO: 5;
   (c) an amino acid sequence that is at least about 90% homologous to an amino acid sequence of SEQ ID NO: 5; or
   (d) a fusion protein comprising a peptide of (a) to (c) above;
   wherein the peptide is capable of interfering with the ability of a virus to use host tRNA$^{LYS3}$ to prime reverse transcription.

2. The peptide of claim 1, wherein said homologous amino acid sequence is at least about 95% homologous to an amino acid sequence of SEQ ID NO: 5.

3. The peptide of claim 1, wherein said peptide contains a D-amino acid.

4. A therapeutic composition comprising the peptide or fusion protein of claim 1 and a pharmaceutically acceptable carrier, diluent or excipient.

5. The peptide of claim 1, wherein said peptide prevents the viral protein from binding to an anticodon stem loop domain of the tRNA$^{LYS3}$.

6. A method of treating a lentivirus infection in a subject in need thereof, comprising administering said subject a peptide of claim 1 in a treatment effective amount.

7. The method of claim 6, wherein said infection is a human immunodeficiency virus (HIV) infection.

8. A method of screening for a compound for treatment of a lentivirus infection, comprising:
   contacting a tRNA$^{LYS3}$ with at least one peptide that interacts with tRNA$^{LYS3}$;
   contacting said tRNA$^{LYS3}$ and said at least one peptide with one or more candidate compounds; and
   identifying the one or more candidate compounds that inhibit the interaction of tRNA$^{LYS3}$ with the at least one peptide, said at least one peptide selected from:
   (a) RVTHHAFLGAHRTVG (SEQ ID NO:5);
   (b) a fragment of 10 or more contiguous amino acids from an amino acid sequence of SEQ ID NO:5;
   (c) an amino acid sequence that is at least about 90% homologous to an amino acid sequence of SEQ ID NO:5; or
   (d) a fusion protein comprising a peptide of (a) to (c) above.

9. The method of claim 8, wherein the tRNA$^{LYS3}$ is an anticodon stem loop domain of tRNA$^{LYS3}$.

10. The method of claim 9 wherein said anticodon stem loop domain of tRNA$^{LYS3}$ contains one or more modified nucleoside bases.

* * * * *